United States Patent
Kori et al.

(10) Patent No.: US 10,444,628 B2
(45) Date of Patent: *Oct. 15, 2019

(54) COMPOUND FOR FORMING ORGANIC FILM, COMPOSITION FOR FORMING ORGANIC FILM, METHOD FOR FORMING ORGANIC FILM, AND PATTERNING PROCESS

(71) Applicant: SHIN-ETSU CHEMICAL CO., LTD., Tokyo (JP)

(72) Inventors: Daisuke Kori, Jyoetsu (JP); Tsutomu Ogihara, Jyoetsu (JP); Takeru Watanabe, Jyoetsu (JP); Yoshinori Taneda, Jyoetsu (JP); Kazunori Maeda, Jyoetsu (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/371,815

(22) Filed: Dec. 7, 2016

(65) Prior Publication Data

US 2017/0184968 A1 Jun. 29, 2017

(30) Foreign Application Priority Data

Dec. 24, 2015 (JP) .................................. 2015-252001

(51) Int. Cl.
*G03F 7/11* (2006.01)
*G03F 7/039* (2006.01)
(Continued)

(52) U.S. Cl.
CPC .............. *G03F 7/094* (2013.01); *C07C 39/23* (2013.01); *C07C 43/215* (2013.01);
(Continued)

(58) Field of Classification Search
None
See application file for complete search history.

(56) References Cited

U.S. PATENT DOCUMENTS 5,155,196 A * 10/1992 Kolb ...................... C07C 41/16
526/247
5,367,043 A * 11/1994 Butler .................... C08G 61/00
528/193
(Continued)

FOREIGN PATENT DOCUMENTS

EP 350747 * 1/1990 ............... C08F 34/02
JP 03-207769 * 9/1991 ............... G03F 7/04
(Continued)

OTHER PUBLICATIONS

Galvez et al., "Water soluble fluorescent-magnetic perylenediimide-containing maghemite-nanoparticles for bimodal MRI/OI imaging"., J. Inorg. Biochem., vol. 117 pp. 205-2011 (2012).*
(Continued)

*Primary Examiner* — Martin J Angebranndt
(74) *Attorney, Agent, or Firm* — Oliff PLC

(57) ABSTRACT

A compound for forming an organic film shown by the formula (1A), $$R\text{-}(X)_{m1} \tag{1A}$$

wherein R represents a single bond or an organic group having 1 to 50 carbon atoms; X represents a group shown by formula (1B); and m1 represents an integer satisfying $2 \leq m1 \leq 10$, (Continued)

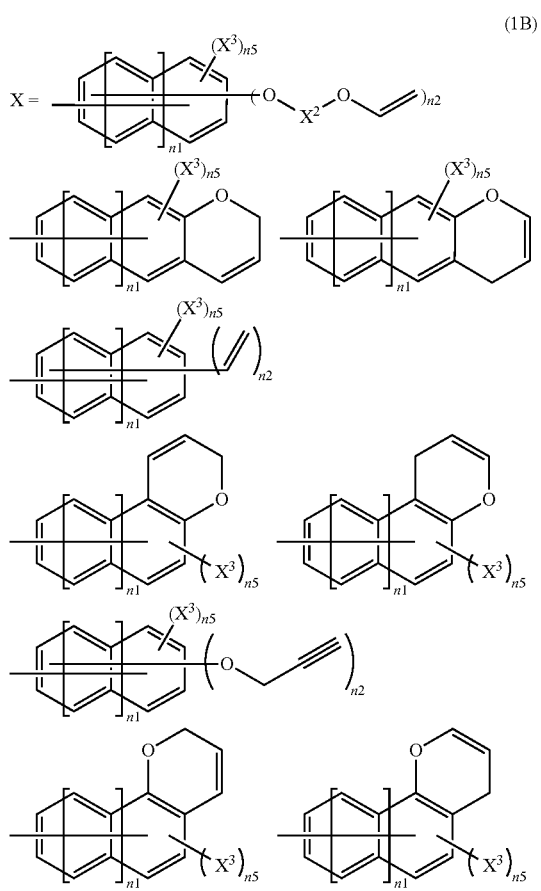

(1B)

wherein $X^2$ represents a divalent organic group having 1 to 10 carbon atoms; n1 represents 0 or 1; n2 represents 1 or 2; $X^3$ represents a group shown by the formula (1C); and n5 represents 0, 1, or 2,

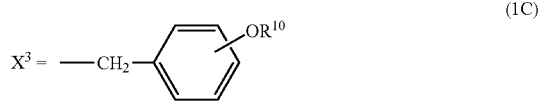

(1C)

wherein $R^{10}$ represents a hydrogen atom or a saturated or unsaturated hydrocarbon group having 1 to 10 carbon atoms, wherein a hydrogen atom of the benzene ring in formula (1C) may be substituted with a methyl group or methoxy group. This compound for forming an organic film can provide organic film composition having good dry etching resistance, heat resistance to 400° C. or higher, high filling and planarizing properties.

17 Claims, 2 Drawing Sheets

(51) Int. Cl.
| | | |
|---|---|---|
| G03F 7/16 | (2006.01) | |
| G03F 7/20 | (2006.01) | |
| G03F 7/30 | (2006.01) | |
| C07C 49/653 | (2006.01) | |
| C07C 49/683 | (2006.01) | |
| H01L 21/311 | (2006.01) | |
| H01L 21/033 | (2006.01) | |
| C07D 311/92 | (2006.01) | |
| C07C 39/23 | (2006.01) | |
| C07C 43/215 | (2006.01) | |
| C07C 43/285 | (2006.01) | |
| H01L 21/30 | (2006.01) | |
| H01L 21/027 | (2006.01) | |
| G03F 7/09 | (2006.01) | |
| C09D 5/00 | (2006.01) | |
| G03F 1/32 | (2012.01) | |
| G03F 7/004 | (2006.01) | |
| G03F 7/32 | (2006.01) | |
| H01L 21/308 | (2006.01) | |
| G03F 7/075 | (2006.01) |

(52) U.S. Cl.
CPC .......... *C07C 43/285* (2013.01); *C07C 49/653* (2013.01); *C07C 49/683* (2013.01); *C07D 311/92* (2013.01); *C09D 5/008* (2013.01); *G03F 1/32* (2013.01); *G03F 7/0045* (2013.01); *G03F 7/039* (2013.01); *G03F 7/0752* (2013.01); *G03F 7/091* (2013.01); *G03F 7/16* (2013.01); *G03F 7/168* (2013.01); *G03F 7/2041* (2013.01); *G03F 7/322* (2013.01); *H01L 21/0274* (2013.01); *H01L 21/0332* (2013.01); *H01L 21/3081* (2013.01); *H01L 21/3086* (2013.01); *C07C 2603/12* (2017.05); *C07C 2603/18* (2017.05); *C07C 2603/40* (2017.05); *C07C 2603/52* (2017.05); *C07C 2603/54* (2017.05); *H01L 21/31116* (2013.01); *H01L 21/31138* (2013.01)

(56) References Cited

U.S. PATENT DOCUMENTS

| | | | | |
|---|---|---|---|---|
| 5,475,074 | A | * | 12/1995 | Matsuoka ............. C08F 212/34 351/159.33 |
| 5,475,133 | A | * | 12/1995 | Douglas ................. C07C 69/92 526/285 |
| 5,876,900 | A | * | 3/1999 | Watanabe ............. G03F 7/0045 430/270.1 |
| 8,501,033 | B2 | | 8/2013 | Southwell et al. |
| 9,728,420 | B2 | | 8/2017 | Kori et al. |
| 9,773,673 | B2 | * | 9/2017 | Park ...................... H01L 21/0337 |
| 9,785,049 | B2 | * | 10/2017 | Hatakeyama ......... G03F 7/0397 |
| 9,804,492 | B2 | * | 10/2017 | Hatakeyama ....... H01L 21/0332 |
| 9,958,781 | B2 | * | 5/2018 | Matsumura ............ G03F 7/11 |
| 10,156,788 | B2 | * | 12/2018 | Hatakeyama ............ G03F 7/11 |
| 2002/0106909 | A1 | | 8/2002 | Kato et al. |
| 2003/0099847 | A1 | | 5/2003 | Cunningham et al. |
| 2005/0255712 | A1 | | 11/2005 | Kato et al. |
| 2006/0019195 | A1 | | 1/2006 | Hatakeyama et al. |
| 2006/0204891 | A1 | | 9/2006 | Hatakeyama |
| 2009/0081595 | A1 | * | 3/2009 | Hatakeyama ......... G03F 7/0397 430/323 |
| 2009/0274978 | A1 | | 11/2009 | Ohashi et al. |
| 2009/0311624 | A1 | | 12/2009 | Horiguchi et al. |
| 2010/0018750 | A1 | | 1/2010 | Schaal et al. |
| 2010/0099044 | A1 | * | 4/2010 | Hatakeyama ........... G03F 7/091 430/285.1 |
| 2011/0236595 | A1 | | 9/2011 | Kodama et al. |
| 2012/0251841 | A1 | | 10/2012 | Southwell et al. |
| 2014/0004465 | A1 | | 1/2014 | Ohnishi et al. |
| 2014/0227887 | A1 | * | 8/2014 | Kim ....................... C08G 61/02 438/781 |
| 2014/0363955 | A1 | * | 12/2014 | Hatakeyama ......... H01L 21/266 438/514 |
| 2015/0322193 | A1 | | 11/2015 | Banach et al. |
| 2015/0337164 | A1 | | 11/2015 | Ohashi et al. |

(56) References Cited

U.S. PATENT DOCUMENTS

| | | | |
|---|---|---|---|
| 2016/0215183 A1 | 7/2016 | Tanaka et al. | |
| 2016/0257842 A1* | 9/2016 | Wakamatsu | C09D 161/14 |
| 2016/0314984 A1 | 10/2016 | Matsumura et al. | |
| 2016/0336189 A1 | 11/2016 | Kori et al. | |
| 2017/0017156 A1 | 1/2017 | Ogihara et al. | |
| 2017/0183531 A1* | 6/2017 | Kori | C09D 155/00 |
| 2018/0011405 A1 | 1/2018 | Watanabe et al. | |

FOREIGN PATENT DOCUMENTS

| | | | | |
|---|---|---|---|---|
| JP | 11-092562 | * | 4/1999 | C08K 5/06 |
| JP | 2002-334869 A | | 11/2002 | |
| JP | 2004-205658 A | | 7/2004 | |
| JP | 2004-205685 A | | 7/2004 | |
| JP | 2005-128509 A | | 5/2005 | |
| JP | 2005-250434 A | | 9/2005 | |
| JP | 2006106214 A | | 4/2006 | |
| JP | 2006-227391 A | | 8/2006 | |
| JP | 2006-233188 A | | 9/2006 | |
| JP | 2006259708 A | | 9/2006 | |
| JP | 2006-285095 A | | 10/2006 | |
| JP | 2006-293298 A | | 10/2006 | |
| JP | 2007-025275 | * | 2/2007 | G03F 7/027 |
| JP | 2007-199653 A | | 8/2007 | |
| JP | 2008158002 A | | 7/2008 | |
| JP | 2009-269953 A | | 11/2009 | |
| JP | 2010-122656 A | | 6/2010 | |
| JP | 2010-271654 | * | 12/2010 | G03F 7/11 |
| JP | 2010-285403 | * | 12/2010 | G03F 7/11 |
| JP | 2011-190336 | * | 9/2011 | C09J 4/00 |
| JP | 4784784 B2 | | 10/2011 | |
| JP | 2012-198527 A | | 10/2012 | |
| JP | 2013-028574 | * | 2/2013 | C07C 41/18 |
| JP | 2014-166988 A | | 9/2014 | |
| JP | 2015-091775 | * | 5/2015 | C07C 43/215 |
| JP | 2016-065526 A | | 4/2016 | |
| JP | 2016-206676 A | | 12/2016 | |
| JP | 6372887 B2 | | 8/2018 | |
| WO | 93/009074 A2 | | 5/1993 | |
| WO | 2004/066377 A1 | | 8/2004 | |

OTHER PUBLICATIONS

Mar. 12, 2018 Office Action issued in U.S. Appl. No. 15/359,323.
Aug. 1, 2018 Office Action Issued in U.S. Appl. No. 15/359,323.
U.S. Appl. No. 15/359,323, filed Nov. 22, 2016 in the name of Kori et al.
Jan. 30, 2019 Office Action issued in U.S. Appl. No. 15/359,323.
Jul. 23, 2019 Office Action issued in Japanese Patent Application No. 2016-218071.
Jul. 16, 2019 Office Action issued in Japanese Patent Application No. 2016-218107.

* cited by examiner (G)

(H)

(I)

(J)

(K)

COMPOUND FOR FORMING ORGANIC FILM, COMPOSITION FOR FORMING ORGANIC FILM, METHOD FOR FORMING ORGANIC FILM, AND PATTERNING PROCESS

BACKGROUND OF THE INVENTION

Field of the Invention

The present invention relates to a compound for forming an organic film for use in multilayer resist for fine processing to manufacture a semiconductor apparatus, etc., or an organic film for planarization to manufacture a semiconductor apparatus, etc. The invention also relates to a composition for forming an organic film containing the compound, a method for forming an organic film using the composition, and a patterning process using the composition.

Description of the Related Art

As LSI advances toward high integration and high processing speed, miniaturization of pattern size is progressing rapidly. Along with the miniaturization, lithography technology has achieved a fine patterning by shortening wavelength of a light source and selecting an appropriate resist composition accordingly. The composition mainly used is a positive photoresist composition for monolayer. The monolayer positive photoresist composition not only allows a resist resin to have a skeleton having etching resistance against dry etching with chlorine- or fluorine-based gas plasma, but also provides a resist mechanism that makes an exposed part soluble, thereby dissolving the exposed part to form a pattern and processing a substrate to be processed, on which the resist composition has been applied, by dry etching using the remaining resist pattern as an etching mask.

However, when the pattern becomes finer, that is, the pattern width is reduced without changing the thickness of the photoresist film to be used, resolution performance of the photoresist film is lowered. In addition, pattern development of the photoresist film with a developer excessively increases a so-called aspect ratio of the pattern, resulting in pattern collapse. Therefore, the photoresist film has been thinned along with the miniaturization of the pattern.

On the other hand, a substrate to be processed has been generally processed by dry etching using a pattern-formed photoresist film as an etching mask. In practice, however, there is no dry etching method capable of providing an absolute etching selectivity between the photoresist film and the substrate to be processed. The resist film is thus damaged and collapses during processing the substrate, and the resist pattern cannot be precisely transferred to the substrate to be processed. Accordingly, higher dry etching resistance has been required in a resist composition along with the miniaturization of the pattern. In the meantime, a resin used for the photoresist composition has been required to have low absorption at the exposure wavelength in order to enhance the resolution. The resin thus shifts to a novolak resin, polyhydroxystyrene, and a resin having an aliphatic polycyclic skeleton as the exposure light shifts from i-line to KrF and ArF, which have shorter wavelength. This shift actually accelerates an etching rate under dry etching condition for processing the substrate, and recent photoresist compositions having high resolution tend to have low etching resistance.

Thus, the substrate to be processed has to be dry etched with a thinner photoresist film having lower etching resistance. The need to provide a composition used in this process and the process itself has become urgent.

A multilayer resist method is one of solutions for these problems. This method is as follows: a middle layer film having a different etching selectivity from a photoresist film (i.e., a resist upper layer film) is placed between the resist upper layer film and a substrate to be processed; a pattern is formed in the resist upper layer film; the pattern is transferred to the middle layer film by dry etching using the resist upper layer film pattern as a dry etching mask; the pattern is further transferred to the substrate to be processed by dry etching using the middle layer film as a dry etching mask.

One of the multilayer resist methods is a three-layer resist method, which can be performed with a typical resist composition used in the monolayer resist method. For example, this three-layer resist method includes the following steps: an organic film containing a novolak resin or the like is formed as a resist underlayer film on a substrate to be processed; a silicon-containing film is formed thereon as a resist middle layer film; a usual organic photoresist film is formed thereon as a resist upper layer film. Since the organic resist upper layer film exhibits an excellent etching selectivity ratio relative to the silicon-containing resist middle layer film when dry etching is performed with fluorine-based gas plasma, the resist upper layer film pattern can be transferred to the silicon-containing resist middle layer film by dry etching with fluorine-based gas plasma. This method allows the pattern to be transferred to the silicon-containing film (resist middle layer film) even using a resist composition that is difficult to form a pattern having a sufficient film thickness for directly processing the substrate to be processed or a resist composition that has insufficient dry etching resistance for processing the substrate. Further, dry etching with oxygen gas plasma or hydrogen gas plasma allows the pattern to be transferred to the organic film (resist underlayer film) containing a novolak resin or the like, which has a sufficient dry etching resistance for processing the substrate. As to the resist underlayer film, many materials are already known as disclosed in Patent Document 1.

In recent years, on the other hand, there is a growing need for an underlayer film having excellent filling and planarizing properties as well as dry etching resistance. For example, when the substrate to be processed used as a base has a fine pattern structure such as hole and trench, the filling property is required to fill the gaps of the pattern without space. In addition, when the substrate to be processed used as a base has steps, or when one wafer contains both a pattern-dense region and a pattern-free region, the surface of the substrate or the wafer requires being planarized by the underlayer film. Planarizing the surface by the underlayer film reduces fluctuation in film thickness of a middle layer film and a resist upper layer film formed thereon, thus increasing a focus margin in lithography or a margin in a subsequent step of processing the substrate to be processed.

To improve the filling and planarizing properties of an underlayer film composition, addition of a liquid additive such as polyether polyol has been proposed (Patent Document 2). However, an organic film formed by this method contains many polyether polyol units, which are inferior in etching resistance. Thus, this film has a markedly lowered etching resistance and is unsuitable for the three-layer resist underlayer film. For this reason, there are demands for a resist underlayer film composition having both excellent filling and planarizing properties and sufficient etching resistance as well as a patterning process using this composition.

Moreover, the organic film composition excellent in filling and planarizing properties is not limited to materials of the underlayer film for multilayer resist. This composition is widely usable also as a planarizing material for manufacturing a semiconductor apparatus, e.g., for planarizing a substrate prior to patterning by nanoimprinting. For global planarizing in the semiconductor apparatus manufacturing process, a CMP process is now generally used. However, the CMP process is costly, so that this composition is also expected to be used for the global planarizing method, instead of CMP.

PRIOR ART DOCUMENTS

Patent Documents

Patent Document 1: Japanese Patent Laid-Open Publication No. 2004-205685
Patent Document 2: Japanese Patent No. 4784784

SUMMARY OF THE INVENTION

The present invention has been accomplished in view of the above circumstances, and an object thereof is to provide a compound for forming an organic film (an organic film compound) that can provide a composition for forming an organic film (an organic film composition) having good dry etching resistance, heat resistance to 400° C. or higher, and high filling and planarizing properties, and further provide a composition for forming an organic film containing the compound, a method for forming an organic film using the composition, and a patterning process using the same.

To achieve this object, the present invention provides a compound for forming an organic film shown by the formula (1A),

(1A)

wherein R represents a single bond or an organic group having 1 to 50 carbon atoms; X represents a group shown by the formula (1B); and m1 represents an integer satisfying $2 \leq m1 \leq 10$,

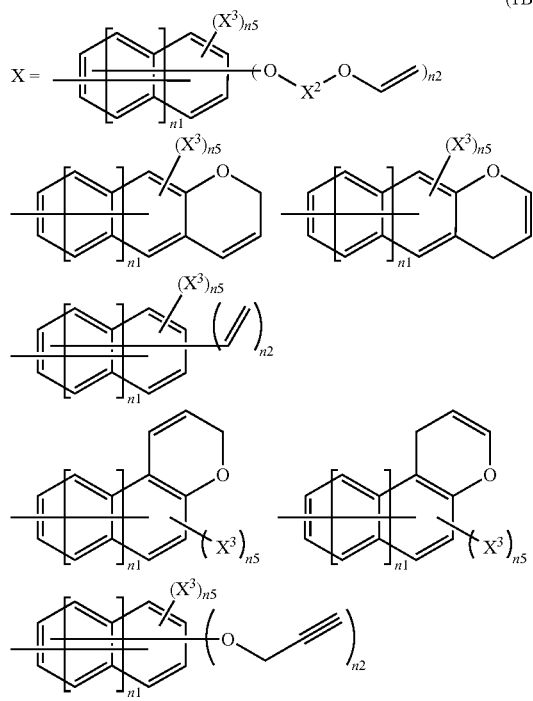

(1B)

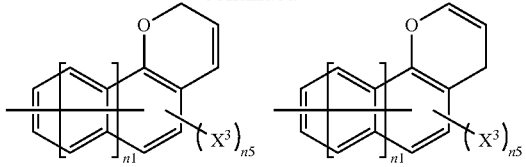

wherein $X^2$ represents a divalent organic group having 1 to 10 carbon atoms; n1 represents 0 or 1; n2 represents 1 or 2; $X^3$ represents a group shown by the formula (1C); and n5 represents 0, 1, or 2,

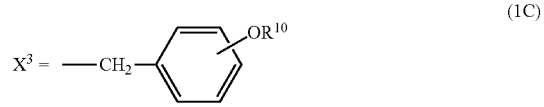

(1C)

wherein $R^{10}$ represents a hydrogen atom or a saturated or unsaturated hydrocarbon group having 1 to 10 carbon atoms, in which a hydrogen atom of the benzene ring in the formula (1C) may be substituted with a methyl group or a methoxy group.

This organic film compound can provide an organic film composition having good dry etching resistance, heat resistance to 400° C. or higher, and high filling and planarizing properties.

It is preferred that the R is an organic group containing one or more quaternary carbon atoms each bonded to four aromatic rings, and one or more of the four aromatic rings bonded to the quaternary carbon atom are the X.

This organic film compound has more excellent heat resistance and exhibits better thermal flowability.

The aromatic rings bonded to the quaternary carbon atom are preferably benzene rings or naphthalene rings, or a combination thereof.

This organic film compound, in which a rigid aromatic ring structure is introduced, can form an organic film having good heat resistance and etching resistance.

Two aromatic rings of the four aromatic rings bonded to the quaternary carbon atom are preferably bonded to each other to form a cyclic structure.

This organic film compound has large steric hindrance and can prevent crystallization. Thus, this compound can form an organic film having excellent heat resistance and etching resistance without reducing thermal flowability.

The compound for forming an organic film preferably satisfies $1.00 \leq Mw/Mn \leq 1.25$ where Mw is a weight average molecular weight and Mn is a number average molecular weight measured by gel permeation chromatography in terms of polystyrene.

Additionally, the compound for forming an organic film preferably has a molecular weight of 2,500 or less, the molecular weight being calculated on the basis of the formula (1A).

When the ratio Mw/Mn and/or the molecular weight calculated on the basis of the formula (1A) are in the above range, the organic film compound can exhibit still better thermal flowability. Thus, a composition containing this compound can favorably fill a fine structure formed on a substrate and form an organic film planarizing the entire substrate.

Furthermore, the present invention provides a composition for forming an organic film, comprising the above-described compound and an organic solvent.

This composition can be applied by spin coating and has good dry etching resistance, heat resistance to 400° C. or higher, and high filling and planarizing properties.

The composition for forming an organic film preferably further comprises either or both of a compound shown by the formula (2A) and a compound shown by the formula (3A),

  (2A)

wherein R is as defined above; X' represents a group shown by the formula (2B); and m2 represents an integer satisfying $1 \leq m2 \leq 5$,

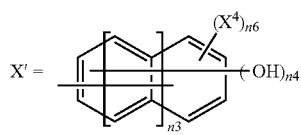  (2B)

wherein n3 represents 0 or 1; n4 represents 1 or 2; $X^4$ represents a group shown by the formula (2C); and n6 represents 0, 1, or 2,

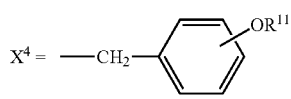  (2C)

wherein $R^{11}$ represents a hydrogen atom or a saturated or unsaturated hydrocarbon group having 1 to 10 carbon atoms, in which a hydrogen atom of the benzene ring in the formula (2C) may be substituted with a methyl group or a methoxy group,

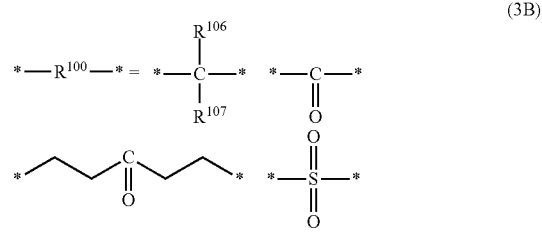  (3B)

wherein * represents a bonding site; $R^{106}$ and $R^{107}$ represent a hydrogen atom or an organic group having 1 to 24 carbon atoms, and $R^{106}$ and $R^{107}$ may be bonded to form a cyclic structure,

  (3C)

wherein * represents a bonding site; and $R^{108}$ represents a hydrogen atom or an organic group having 1 to 15 carbon atoms.

This composition can form an organic film having better adhesiveness to not only a silicon substrate but also a structure substrate formed of silicon oxide or silicon nitride, or a hard mask composed of titanium nitride or the like.

The organic solvent is preferably a mixture of one or more organic solvents having a boiling point of lower than 180° C. and one or more organic solvents having a boiling point of 180° C. or higher.

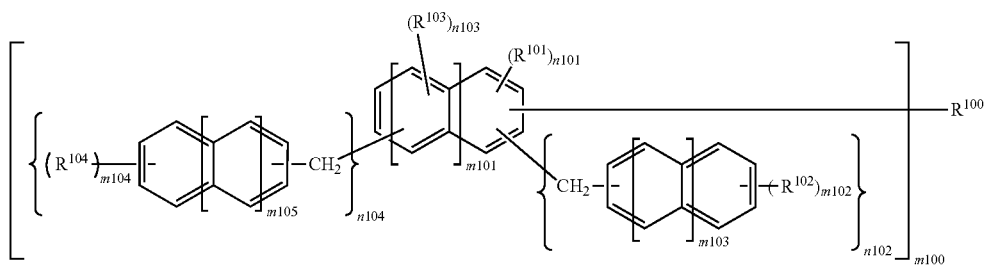  (3A)

wherein $R^{101}$, $R^{102}$, $R^{103}$, and $R^{104}$ independently represent a hydroxyl group; m100 represents 1, 2, or 3; $R^{100}$ represents a hydrogen atom or a hydroxyl group when m100 is 1, $R^{100}$ represents a single bond or a group shown by the formula (3B) when m100 is 2, and $R^{100}$ represents a group shown by the formula (3C) when m100 is 3; a hydrogen atom of the aromatic ring in the formula (3A) may be substituted with a methyl group, a methoxy group, a hydroxymethyl group, or a methoxymethyl group; m101 represents 0 or 1, m102 represents 1 or 2; m103 represents 0 or 1; m104 represents 1 or 2; m105 represents 0 or 1; when m101 is 0, n101 and n102 represent an integer satisfying $0 \leq n101 \leq 3$, $0 \leq n102 \leq 3$, and $1 \leq n101+n102 \leq 4$, and when m101 is 1, n101, n102, n103, and n104 represent an integer satisfying $0 \leq n101 \leq 2$, $0 \leq n102 \leq 2$, $0 \leq n103 \leq 2$, $0 \leq n\psi \leq 2$, and $2 \leq n101+n102+n103+n104 \leq 8$, The organic film composition containing such organic solvents improves its thermal flowability and thus has higher filling and planarizing properties.

Furthermore, the present invention provides a method for forming an organic film that functions as an organic planarizing film used in a semiconductor apparatus manufacturing process, the method comprising: applying the above-described composition for forming an organic film on a substrate to be processed by spin coating; and heating the substrate, on which the composition has been applied, at 100° C. to 600° C. for 10 to 600 seconds to form a cured film.

The heat treatment under the above condition facilitates the planarization by thermal flow and the crosslinking reaction, thus enabling the formation of an organic film without mixing with an overlying film.

Furthermore, the present invention provides a method for forming an organic film that functions as an organic planarizing film used in a semiconductor apparatus manufacturing process, the method comprising: applying the above-described composition for forming an organic film on a substrate to be processed by spin coating; and heating the substrate, on which the composition has been applied, under an atmosphere having an oxygen concentration of 0.1% to 21% to form a cured film.

When the composition is baked in such oxygen atmosphere, an organic film sufficiently cured can be formed.

The substrate to be processed preferably has steps or a structure with a height of 30 nm or more.

The inventive organic film composition, which has excellent filling and planarizing properties, is especially useful for forming a flat organic film on such a substrate to be processed.

Furthermore, the present invention provides a patterning process comprising: forming an organic film on a body to be processed from the above-described composition for forming an organic film; forming a resist underlayer film on the organic film from a resist underlayer film composition containing a silicon atom; forming a resist upper layer film on the resist underlayer film from a resist upper layer film composition composed of a photoresist composition; forming a circuit pattern in the resist upper layer film; transferring the pattern to the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

Furthermore, the present invention provides a patterning process comprising: forming an organic film on a body to be processed from the above-described composition for forming an organic film; forming a resist underlayer film on the organic film from a resist underlayer film composition containing a silicon atom; forming an organic antireflective film on the resist underlayer film; forming a resist upper layer film on the organic antireflective film from a resist upper layer film composition composed of a photoresist composition; forming a circuit pattern in the resist upper layer film; transferring the pattern to the organic antireflective film and the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

Furthermore, the present invention provides a patterning process comprising: forming an organic film on a body to be processed from the above-described composition for forming an organic film; forming an inorganic hard mask selected from a silicon oxide film, a silicon nitride film, and a silicon oxynitride film on the organic film; forming a resist upper layer film on the inorganic hard mask from a resist upper layer film composition composed of a photoresist composition; forming a circuit pattern in the resist upper layer film; transferring the pattern to the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

Furthermore, the present invention provides a patterning process comprising: forming an organic film on a body to be processed from the above-described composition for forming an organic film; forming an inorganic hard mask selected from a silicon oxide film, a silicon nitride film, and a silicon oxynitride film on the organic film; forming an organic antireflective film on the inorganic hard mask; forming a resist upper layer film on the organic antireflective film from a resist upper layer film composition composed of a photoresist composition; forming a circuit pattern in the resist upper layer film; transferring the pattern to the organic antireflective film and the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

In this manner, the inventive organic film composition can be suitably used for various patterning processes such as a 3-layer resist process using a silicon-containing resist underlayer film or an inorganic hard mask, or a 4-layer resist additionally using an organic antireflective film. Such patterning processes of the present invention can transfer and form the circuit pattern of the resist upper layer film to the body to be processed with high precision.

The inorganic hard mask is preferably formed by a CVD method or an ALD method.

In the inventive patterning processes, such methods can be used to form the inorganic hard mask.

The circuit pattern is preferably formed by a photolithography with a wavelength ranging from 10 nm to 300 nm, a direct drawing with electron beam, a nanoimprinting, or a combination thereof.

Additionally, the circuit pattern is preferably developed by alkaline development or development with an organic solvent.

In the inventive patterning processes, such means can be employed to form and develop the circuit pattern.

The body to be processed is preferably a semiconductor apparatus substrate or the semiconductor apparatus substrate coated with any of a metal film, a metal carbide film, a metal oxide film, a metal nitride film, a metal oxycarbide film, and a metal oxynitride film.

Additionally, the metal of the body to be processed is preferably silicon, titanium, tungsten, hafnium, zirconium, chromium, germanium, copper, silver, gold, aluminum, indium, gallium, arsenic, palladium, iron, tantalum, iridium, molybdenum, or an alloy thereof.

In the inventive patterning processes, the above body can be processed to form a pattern.

As mentioned above, the present invention can provide an organic film composition having high filling and planarizing properties, and an organic film compound useful for the composition. In addition, the inventive organic film composition is excellent in properties such as heat resistance and etching resistance besides the filling and planarizing properties. Thus, the composition is extremely useful as an organic film material for multilayer resist processes such as a 2-layer resist process, a 3-layer resist process using a silicon-containing resist underlayer film or an inorganic hard mask, or a 4-layer resist using silicon-containing resist underlayer film or an inorganic hard mask and an organic antireflective film, or as a planarizing material for manufacturing a semiconductor apparatus. In addition, the inventive methods for forming an organic film can form a very flat organic film having sufficient resistance to an organic solvent on a substrate to be processed. In addition, the inventive patterning processes can form a fine pattern in a body to be processed with high precision, according to the multilayer resist process.

DETAILED DESCRIPTION OF THE PREFERRED EMBODIMENTS

Figure 1:
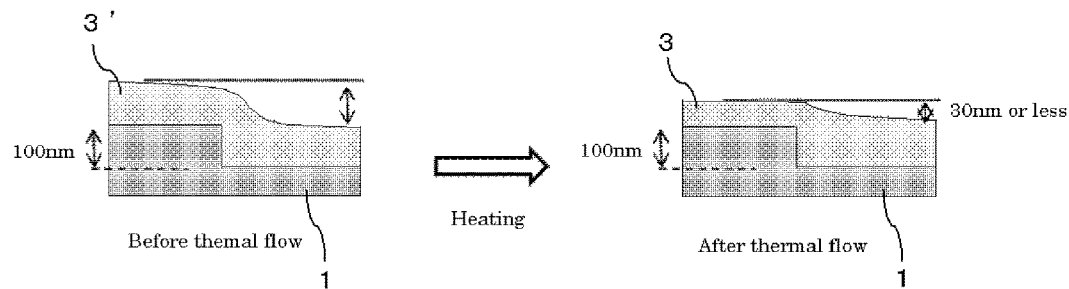
FIG. 1 is an explanatory view of planarizing property in the present invention.

As mentioned above, it has been desired to develop an organic film composition having good dry etching resistance, heat resistance to 400° C. or higher, and high filling and planarizing properties and an organic film compound useful for the composition.

Generally, an organic film is formed by dissolving an organic film compound in an organic solvent to form a composition, applying the composition on a substrate on which a semiconductor device, wiring, and other structure have been formed, and baking the composition. The composition just after the application forms a coating shaped along the structure on the substrate. When the coating is baked, the organic solvent is almost evaporated before curing, and the organic film compound remaining on the substrate forms an organic film. In this context, the present inventors considered that if the organic film compound remaining on the substrate has sufficient thermal flowability, the uneven shape just after the application can be planarized by thermal flow, and a flat film can be formed. The inventors then diligently conducted studies and found that an organic film compound shown by the formula (1A) has good thermal flowability and thus can provide an organic film composition having high filling and planarizing properties, good dry etching resistance, and heat resistance to 400° C. or higher, thereby bringing the present invention to completion.

That is, the present invention is an organic film compound shown by the formula (1A), $$R-(-X)_{m1} \quad (1A)$$

wherein R represents a single bond or an organic group having 1 to 50 carbon atoms; X represents a group shown by the formula (1B); and m1 represents an integer satisfying $2 \leq m1 \leq 10$,

[Structural formulas for X including naphthalene-based groups with $(X^3)_{n5}$ substituents]

wherein $X^2$ represents a divalent organic group having 1 to 10 carbon atoms; n1 represents 0 or 1; n2 represents 1 or 2; $X^3$ represents a group shown by the formula (1C); and n5 represents 0, 1, or 2, $$X^3 = -CH_2- \text{[phenyl]} -OR^{10} \quad (1C)$$

wherein $R^{10}$ represents a hydrogen atom or a saturated or unsaturated hydrocarbon group having 1 to 10 carbon atoms, in which a hydrogen atom of the benzene ring in the formula (1C) may be substituted with a methyl group or a methoxy group.

Hereinafter, the present invention will be described in detail, but the present invention is not limited thereto.

<Organic Film Compound>

The inventive organic film compound is shown by the formula (1A).

Illustrative examples of X in the formula (1A) include the following groups.

-continued
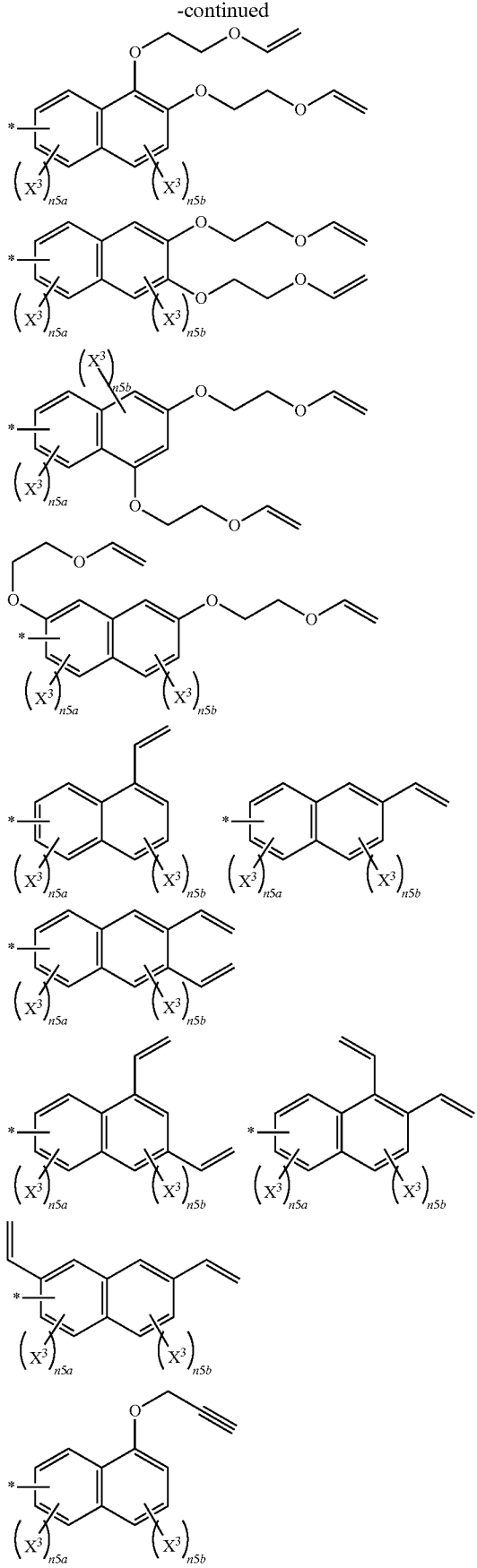
-continued
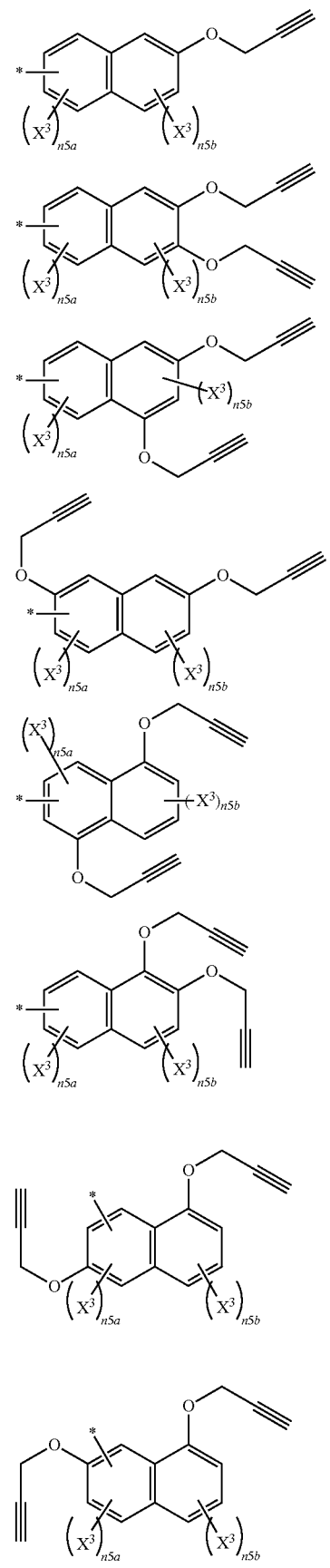

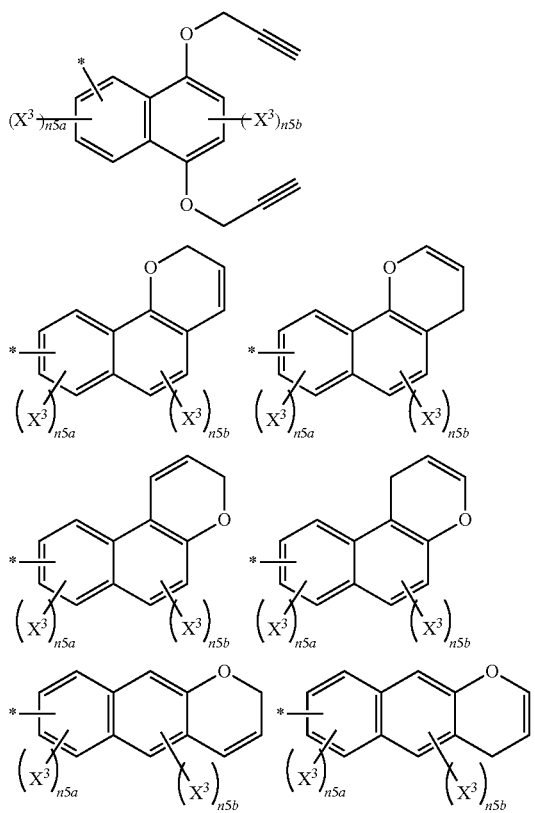
wherein * represents a bonding site to R; $X^3$ is as defined above; and n5a and n5b represent 0, 1, or 2 and satisfy n5a+n5b=n5.
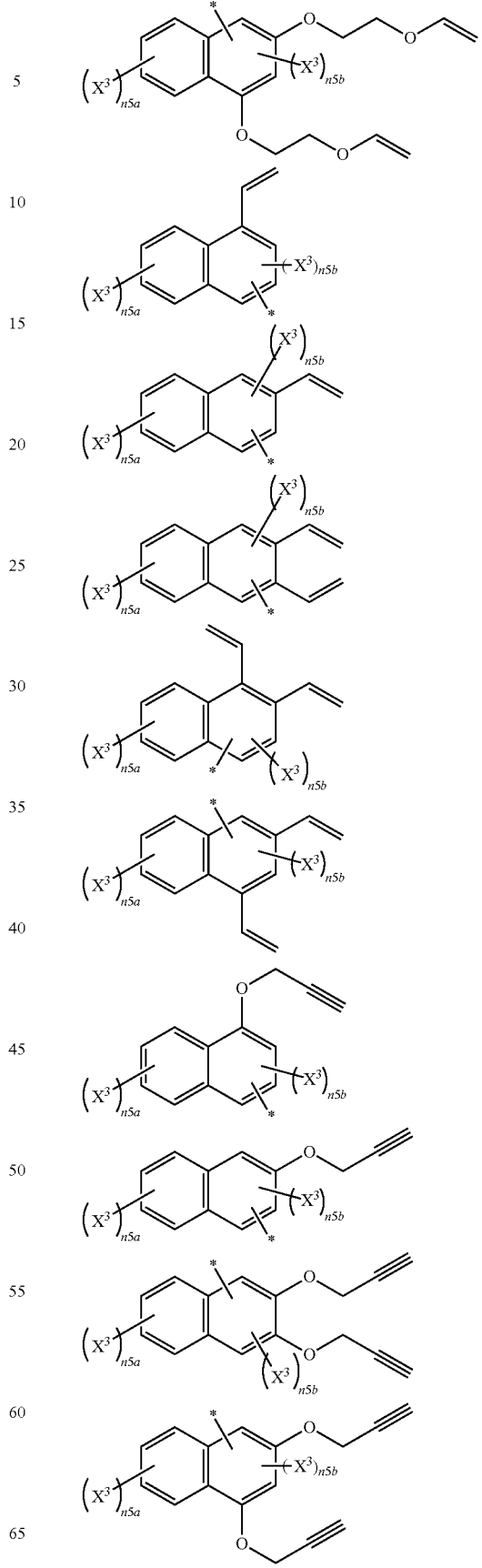

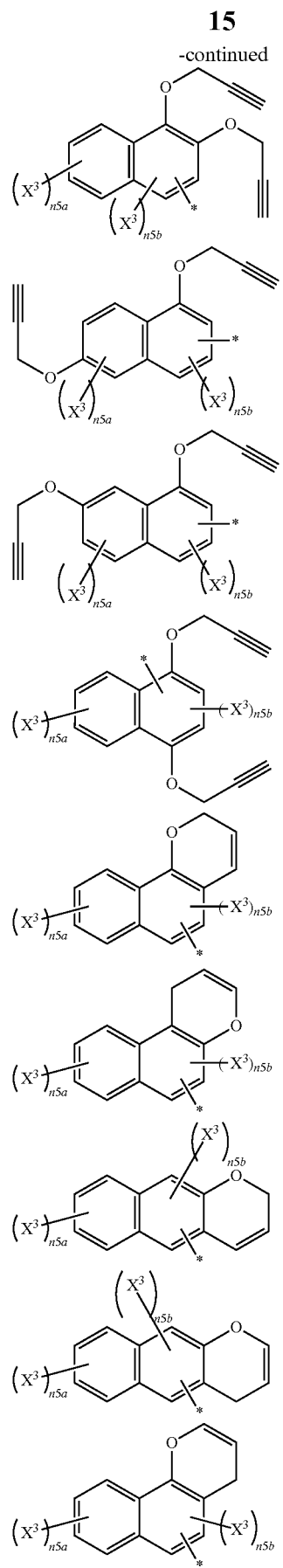
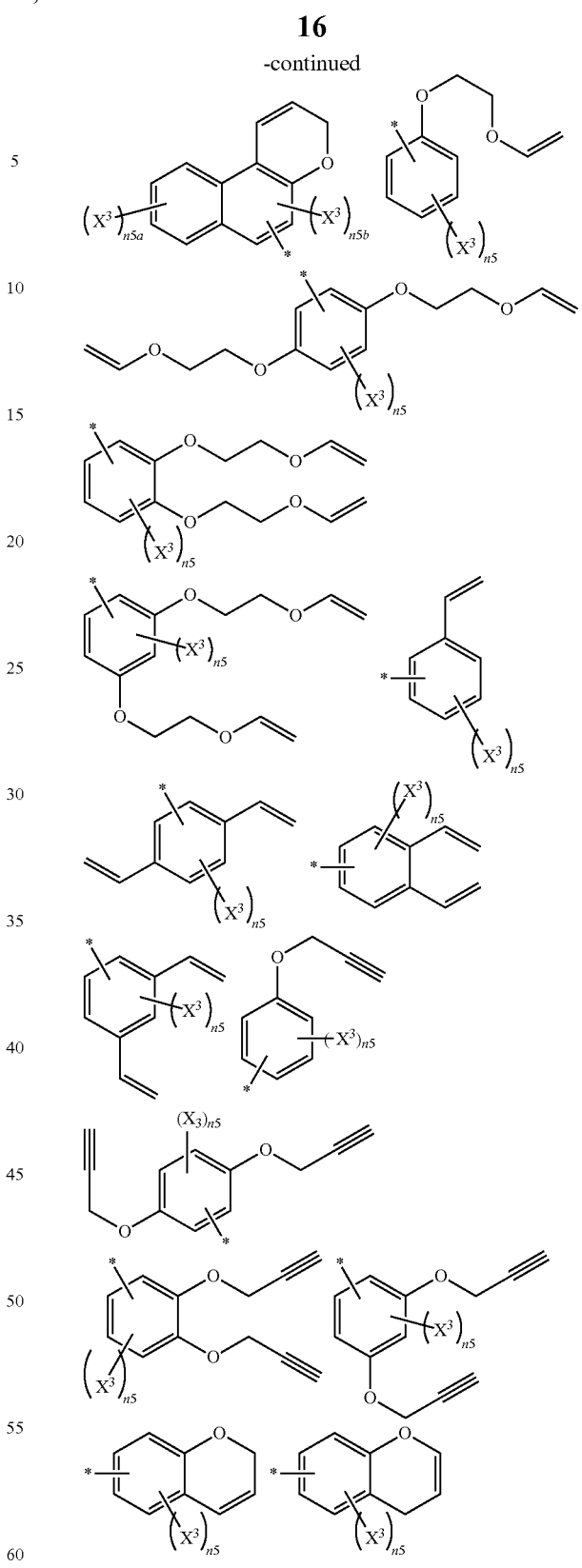
wherein * represents a bonding site to R; $X^3$ is as defined above; and n5a and n5b represent 0, 1, or 2 and satisfy n5a+n5b=n5.
Illustrative examples of $X^2$ in the formula (1B) include the following groups.

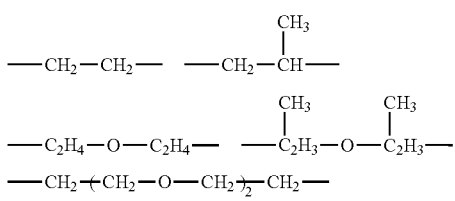

Illustrative examples of $R^{10}$ in the formula (1C) include linear or branched alkyl groups such as a methyl group, an ethyl group, and an isopropyl group; alicyclic hydrocarbon groups such as a cyclopentyl group, a cyclohexyl group, and norbornyl group; linear or branched alkenyl groups such as a vinyl group and a propenyl group; linear or branched alkynyl groups such as an ethynyl group and a propargyl group; and aryl groups such as a phenyl group and a tolyl group.

Illustrative examples of the inventive organic film compound shown by the formula (1A) include the following compounds.

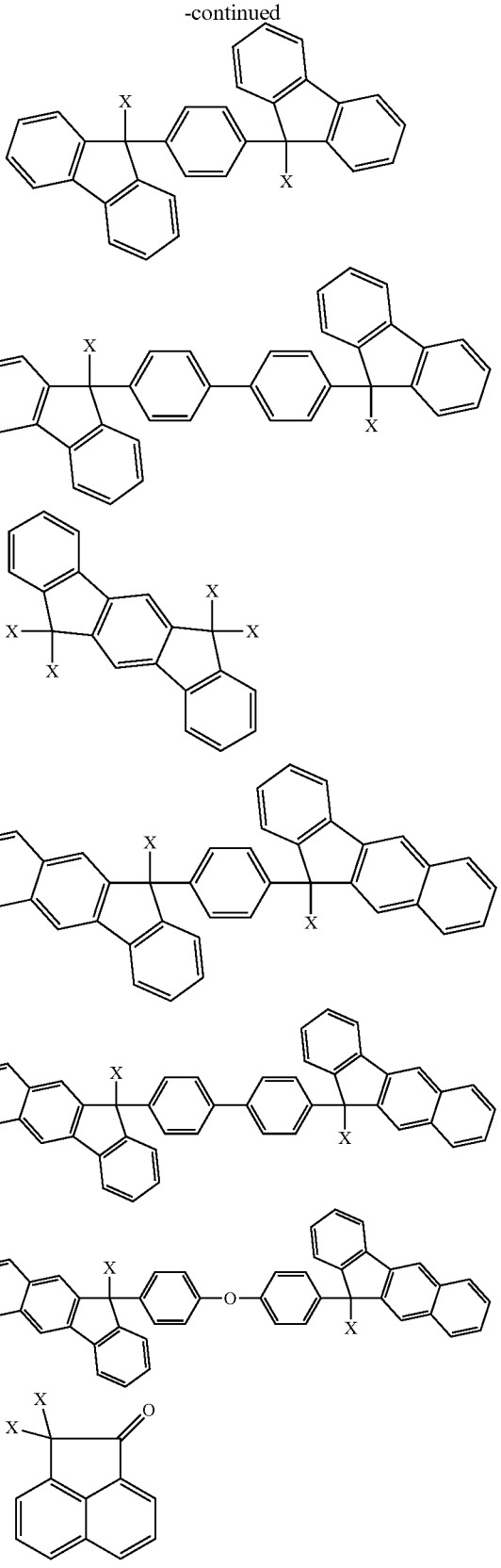

wherein X is as defined above.

It is preferred that R in the formula (1A) is an organic group containing one or more quaternary carbon atoms each bonded to four aromatic rings, and one or more of the four aromatic rings bonded to the quaternary carbon atom are X (i.e., aromatic rings in the formula (1B)). This organic film compound has more excellent heat resistance and exhibits better thermal flowability.

The aromatic rings bonded to the quaternary carbon atom are preferably benzene rings or naphthalene rings, or a combination thereof. This organic film compound, in which a rigid aromatic ring structure is introduced, can form an organic film having good heat resistance and etching resistance.

Two aromatic rings of the four aromatic rings bonded to the quaternary carbon atom are preferably bonded to each other to form a cyclic structure. This organic film compound has large steric hindrance and can prevent crystallization. Thus, this compound can form an organic film having excellent heat resistance and etching resistance without reducing thermal flowability.

The inventive organic film compound preferably satisfies 1.00≤Mw/Mn≤1.25 (the ratio Mw/Mn means dispersibility), in which Mw is a weight average molecular weight and Mn is a number average molecular weight measured by gel permeation chromatography in terms of polystyrene. The organic film compound having such a small dispersibility (a narrow molecular weight distribution) can exhibit still better thermal flowability. Thus, a composition containing this compound can favorably fill a fine structure formed on a substrate and form an organic film planarizing the entire substrate.

Additionally, the inventive organic film compound preferably has a molecular weight of 2,500 or less that is calculated on the basis of the formula (1A). The organic film compound having such a molecular weight can exhibit still better thermal flowability. Thus, a composition containing this compound can favorably fill a fine structure formed on a substrate and form an organic film planarizing the entire substrate.

As described above, the inventive organic film compound can provide an organic film composition having good dry etching resistance, heat resistance to 400° C. or higher, and high filling and planarizing properties.

In the present invention, the planarizing property means a property of planarizing the surface of a substrate. For example, a composition containing the inventive organic film compound can reduce a height of step in a substrate 1 from 100 nm to 30 nm or less, as shown in FIG. 1, by applying the organic film composition 3' on the substrate 1 and heating it to form an organic film 3. The step shape shown in FIG. 1 is a typical example of the step shape in a substrate for manufacturing a semiconductor apparatus, and the step shape that can be planarized by the composition containing the inventive organic film compound is not limited thereto, of course.

<Organic Film Composition>

Furthermore, the present invention provides a composition for forming an organic film, containing the above-described organic film compound and an organic solvent. The used inventive organic film composition may be one organic film compound alone or two or more organic film compounds in combination.

The organic solvent is preferably a solvent that can dissolve the inventive organic film compound and additives such as an acid generator, a crosslinking agent, and a surfactant described later. More specifically, an organic solvent having a boiling point of lower than 180° C. (hereinafter, also referred to as a "low-boiling point solvent"), such as solvents disclosed in paragraphs (0091) and (0092) of Japanese Patent Laid-Open Publication No. 2007-199653, may be used. Above all, propylene glycol monomethyl ether acetate, propylene glycol monomethyl ether, 2-heptanone, cyclopentanone, cyclohexanone, and a mixture of two or more kinds thereof are preferably used.

Such a composition can be applied by spin coating. In addition, this organic film composition contains the inventive organic film compound and thus has good dry etching resistance, heat resistance to 400° C. or higher, and high filling and planarizing properties.

Moreover, the inventive organic film composition may contain an organic solvent in which an organic solvent having a boiling point of 180° C. or higher (hereinafter, also referred to as a "high-boiling point solvent") is added to the above-mentioned low-boiling point solvent (i.e., a mixture of the low-boiling point solvent and the high-boiling point solvent). As the high-boiling point solvent, any solvent that can dissolve the organic film compound, such as hydrocarbons, alcohols, ketones, esters, ethers, and chlorinated solvents, can be used, without particular limitation. Illustrative examples thereof include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol n-butyl ether, triethylene glycol butylmethyl ether, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol methyl-n-propyl ether, dipropylene glycol methyl ether acetate, 1,4-butanediol diacetate, 1,3-butylene glycol diacetate, 1,6-hexanediol diacetate, and γ-butyrolactone. These solvents may be used alone or in combination.

The high-boiling point solvent may be appropriately selected, for example, from the above solvents, according to the temperature at which the organic film composition is subjected to the heat treatment. The boiling point of the high-boiling point solvent is preferably 180° C. to 300° C., more preferably 200° C. to 300° C. This boiling point prevents an excessive evaporation rate at baking (heat treatment) due to low boiling point, providing sufficient thermal flowability. Moreover, the solvent having such a boiling point does not remain in the film without evaporating after baking due to high boiling point, and thus does not affect physical properties of the film, such as etching resistance.

When the high-boiling point solvent is used, the formulation amount of the high-boiling point solvent is preferably 1 to 30 parts by mass based on 100 parts by mass of the low-boiling point solvent. When the formulation amount is in this range, there is no fear of insufficient thermal flowability at baking due to lack of the amount, as well as there is no fear of deterioration of physical properties of the film, such as etching resistance, due to excess amount.

Such an organic film composition can achieve higher filling and planarizing properties since thermal flowability of the organic film compound is improved by addition of the high-boiling point solvent.

The inventive organic film composition preferably further contains either or both of a compound shown by the formula (2A) and a compound shown by the formula (3A),

(2A)

wherein R is as defined above; X' represents a group shown by the formula (2B); and m2 represents an integer satisfying $1 \leq m2 \leq 5$,

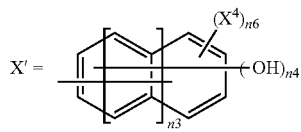
(2B)

wherein n3 represents 0 or 1; n4 represents 1 or 2; $X^4$ represents a group shown by the formula (2C); and n6 represents 0, 1, or 2,

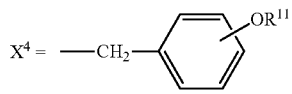
(2C)

wherein $R^{11}$ represents a hydrogen atom or a saturated or unsaturated hydrocarbon group having 1 to 10 carbon atoms, in which a hydrogen atom of the benzene ring in the formula (2C) may be substituted with a methyl group or a methoxy group, and n104 represent an integer satisfying $0 \leq n101 \leq 2$, $0 \leq n102 \leq 2$, $0 \leq n103 \leq 2$, $0 \leq n104 \leq 2$, and $2 \leq n101+n102+n103+n104 \leq 8$,

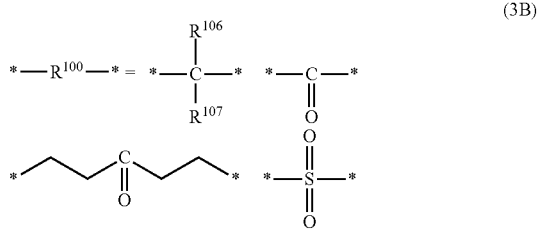
(3B)

wherein * represents a bonding site; $R^{106}$ and $R^{107}$ represent a hydrogen atom or an organic group having 1 to 24 carbon atoms, and $R^{106}$ and $R^{107}$ may be bonded to form a cyclic structure,

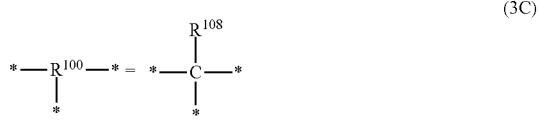
(3C)

wherein * represents a bonding site; and $R^{108}$ represents a hydrogen atom or an organic group having 1 to 15 carbon atoms.

Examples of the compound shown by the formula (2A) include compounds described as examples of the inventive organic film compound shown by the formula (1A) in which X is substituted with X'.

Examples of the compound shown by the formula (3A) include the following compounds. Any hydrogen atom on the aromatic rings of the following compounds may be substituted with a methyl group, a methoxy group, a hydroxymethyl group, or a methoxymethyl group.

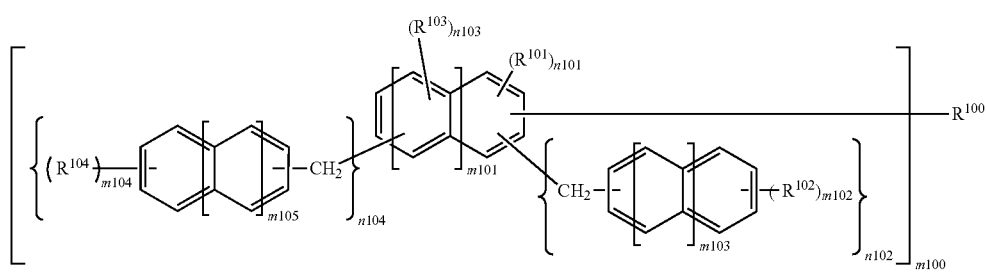
(3A)

wherein $R^{101}$, $R^{102}$, $R^{103}$, and $R^{104}$ independently represent a hydroxyl group; m100 represents 1, 2, or 3; $R^{100}$ represents a hydrogen atom or a hydroxyl group when m100 is 1, $R^{100}$ represents a single bond or a group shown by the formula (3B) when m100 is 2, and $R^{100}$ represents a group shown by the formula (3C) when m100 is 3; a hydrogen atom of the aromatic ring in the formula (3A) may be substituted with a methyl group, a methoxy group, a hydroxymethyl group, or a methoxymethyl group; m101 represents 0 or 1, m102 represents 1 or 2; m103 represents 0 or 1; m104 represents 1 or 2; m105 represents 0 or 1; when m101 is 0, n101 and n102 represent an integer satisfying $0 \leq n101 \leq 3$, $0 \leq n102 \leq 3$, and $1 \leq n101+n102 \leq 4$, and when 101 is 1, n101, n102, n103,

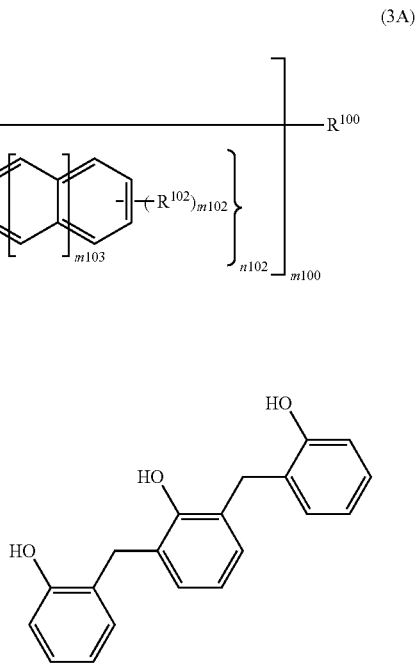

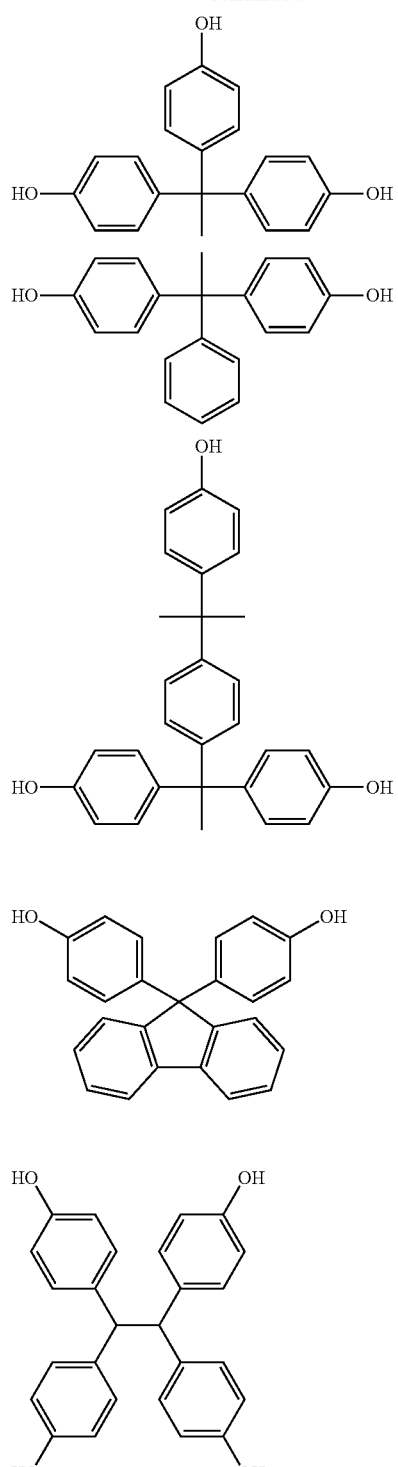
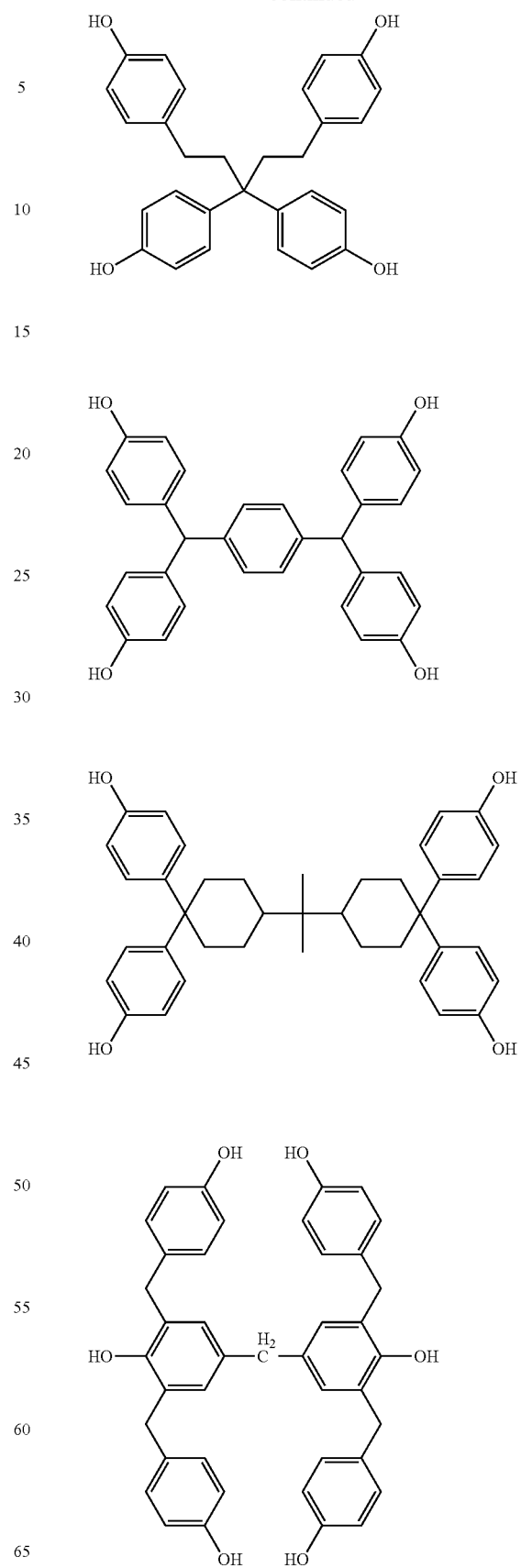

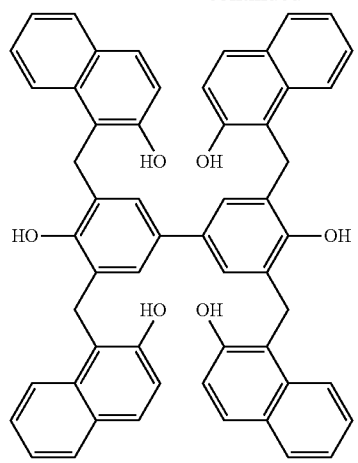
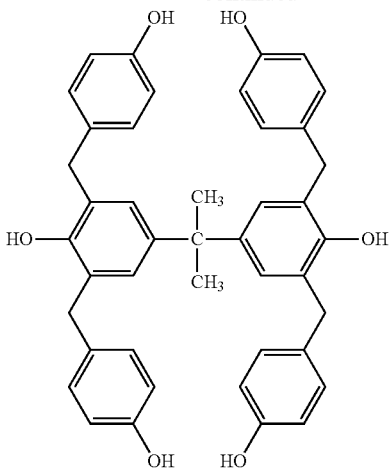
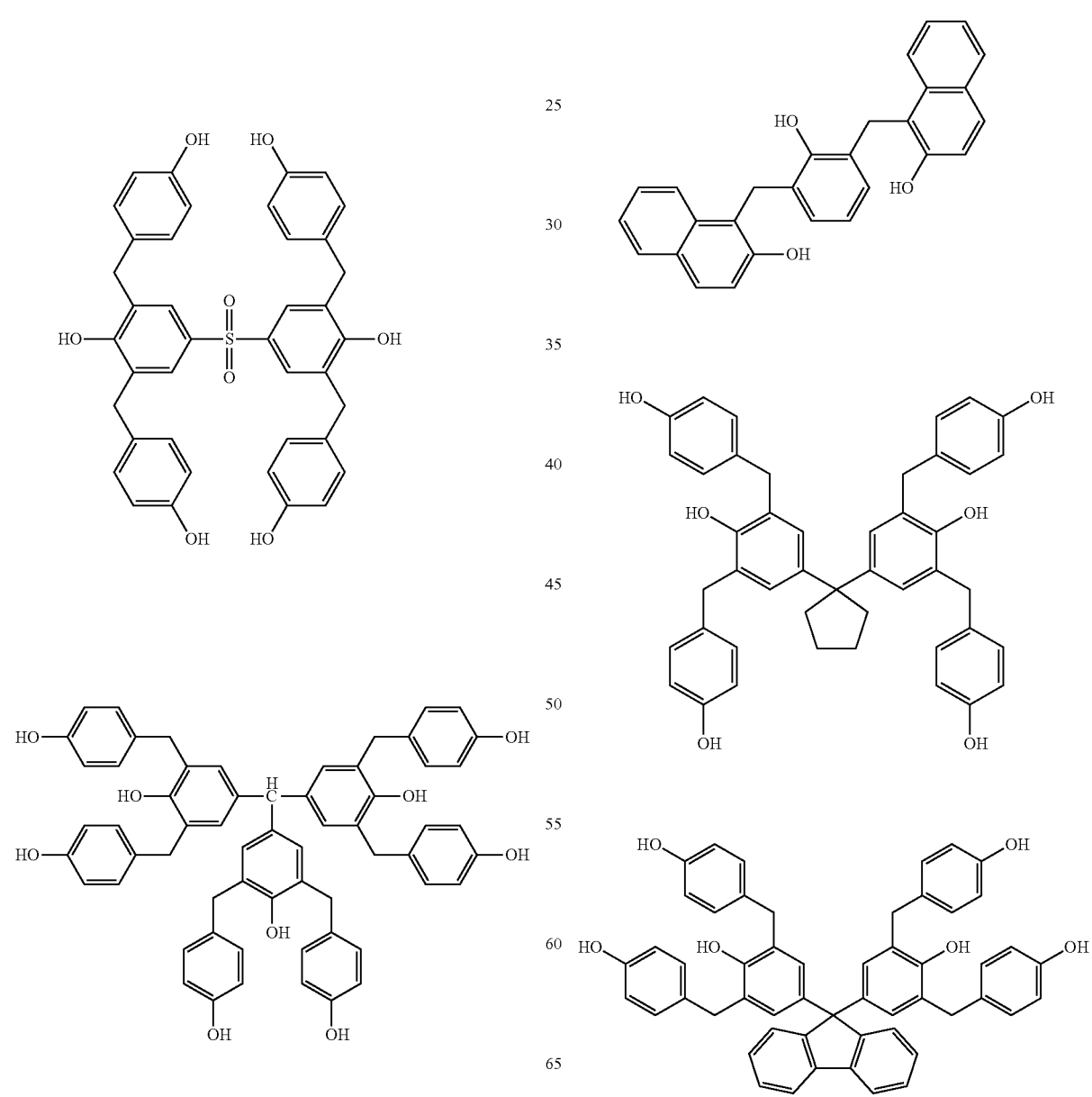

27
-continued
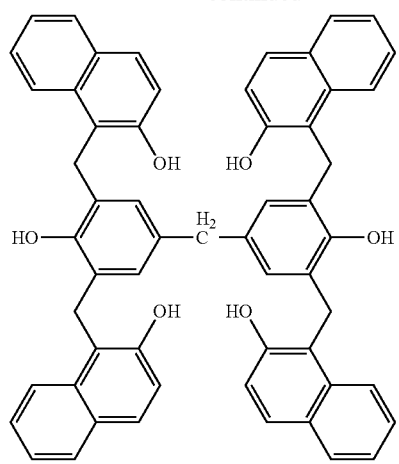
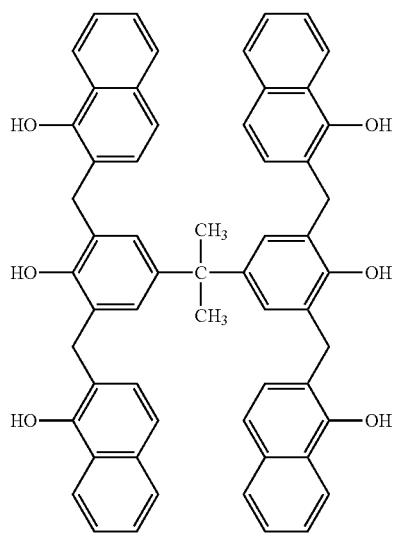
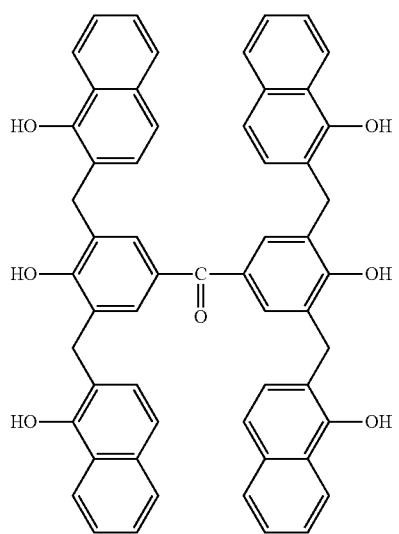
28
-continued
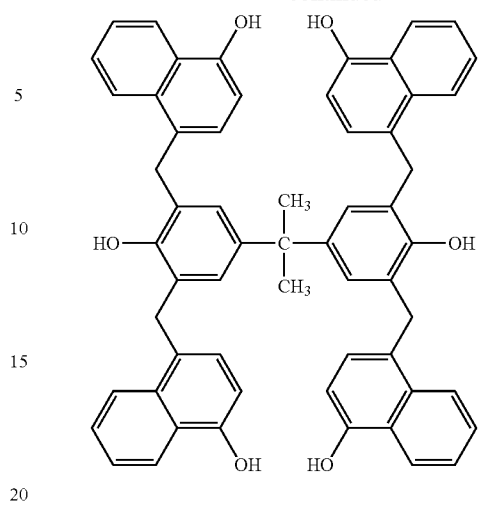
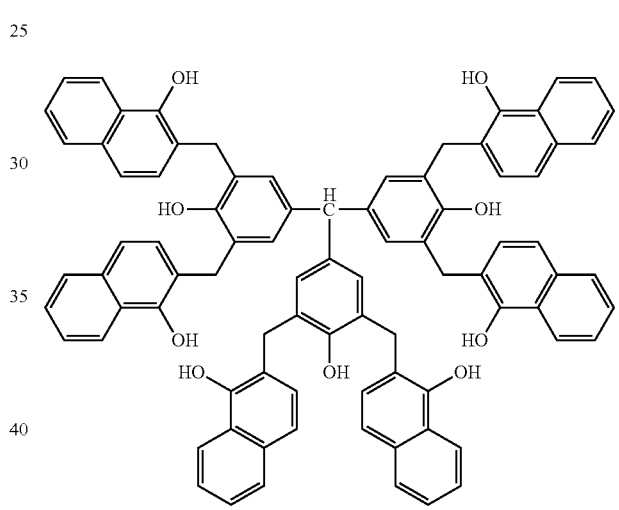
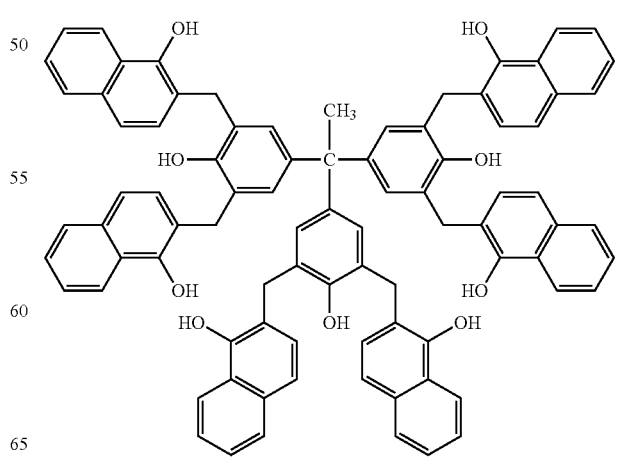

29
-continued
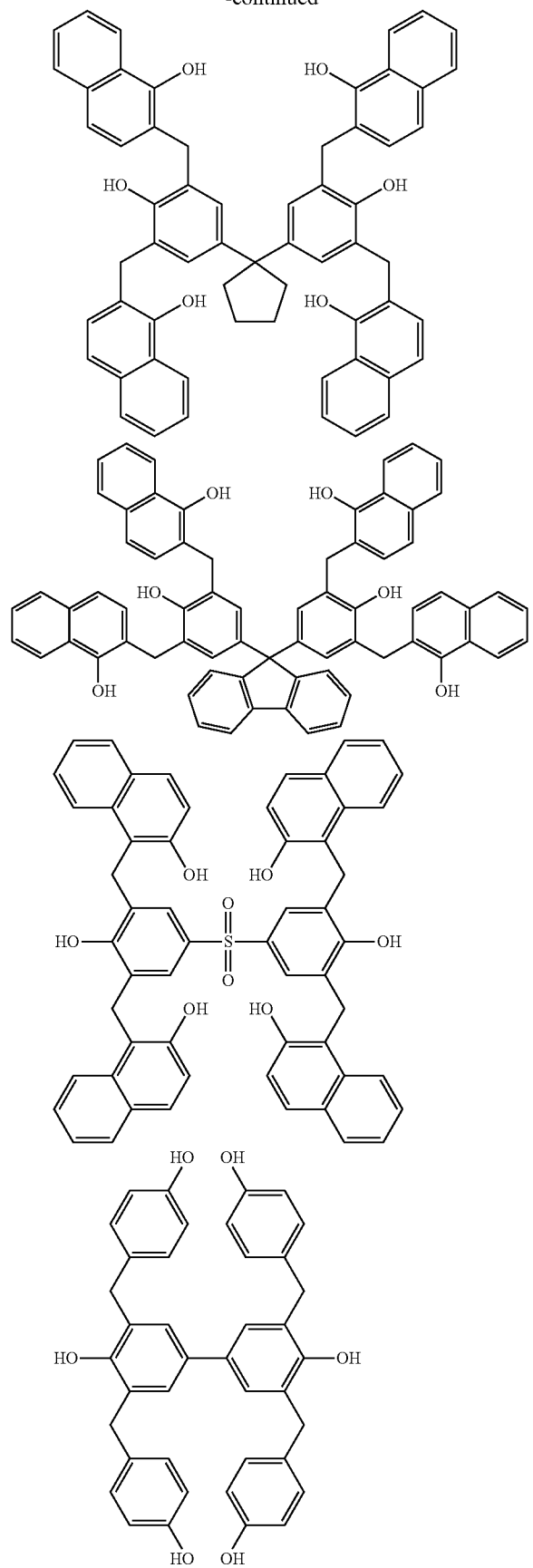
30
-continued
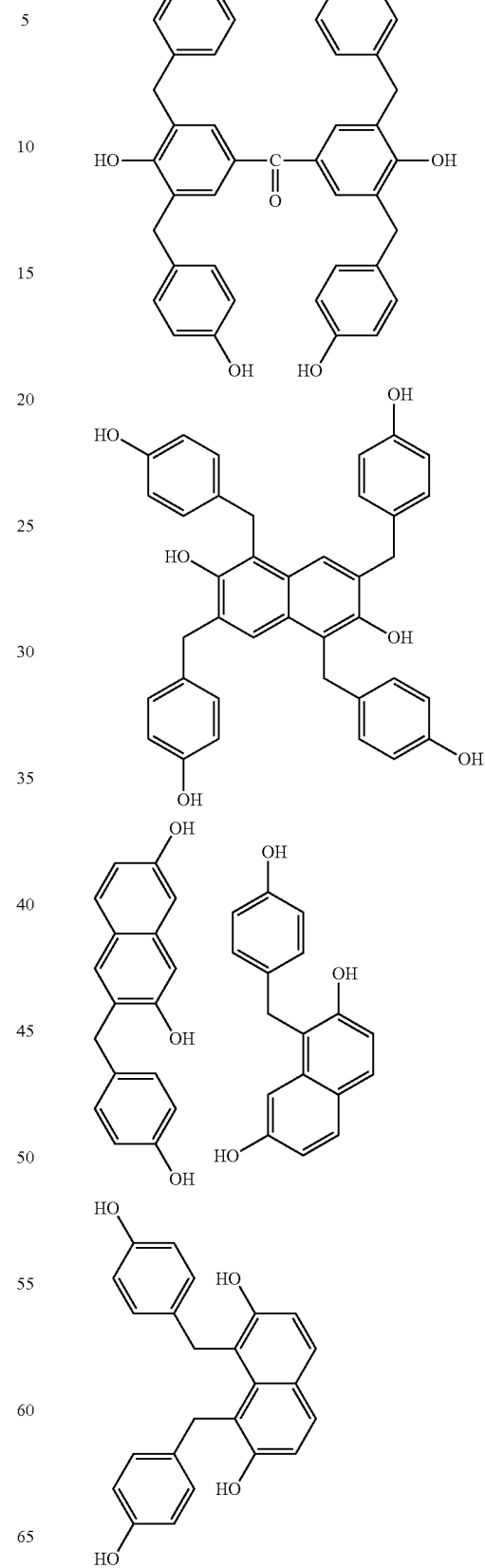

31
-continued
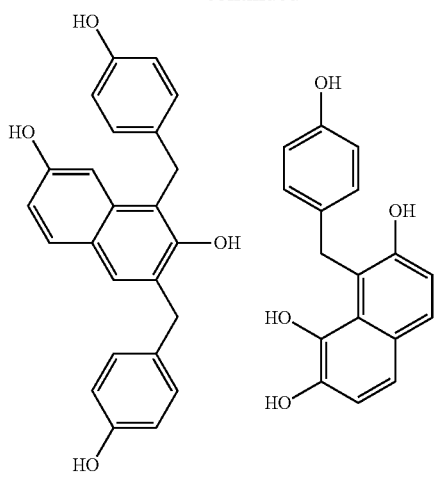
32
-continued
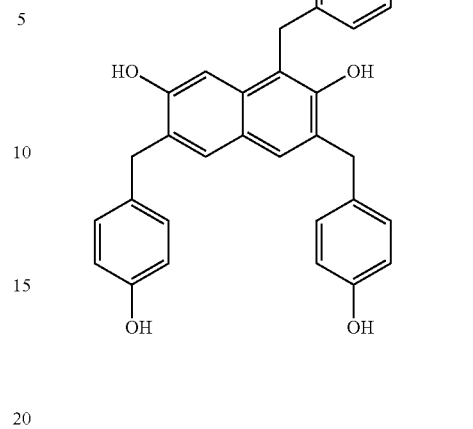
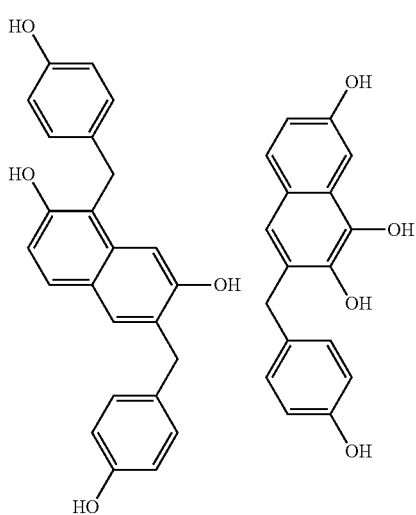
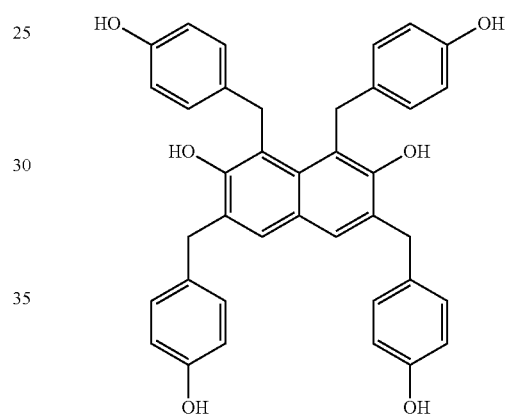
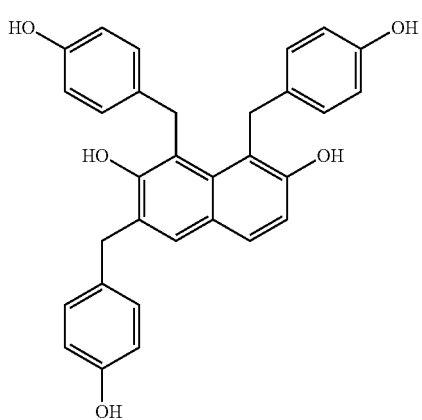
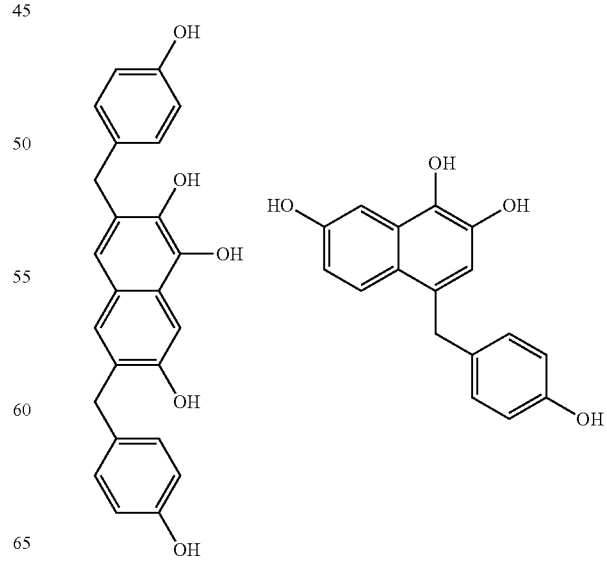

33
-continued
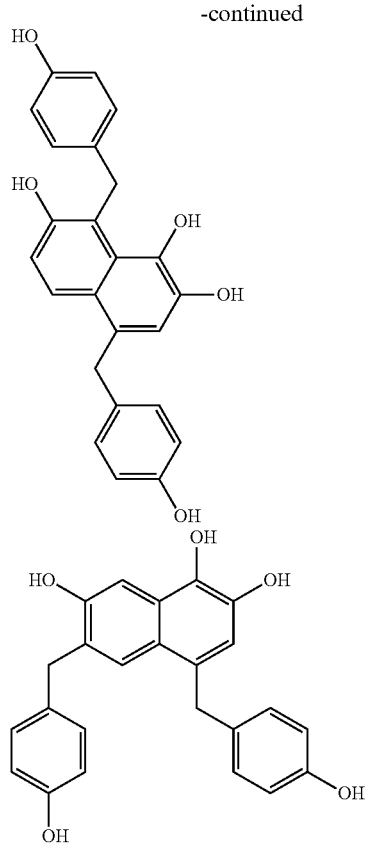
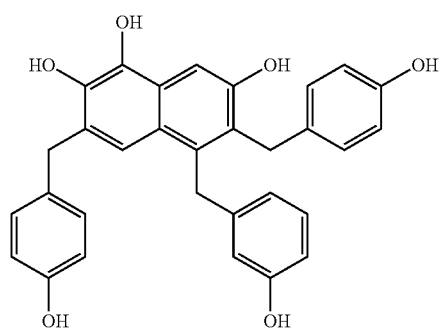
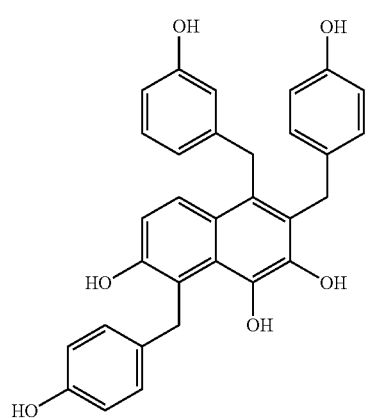
34
-continued
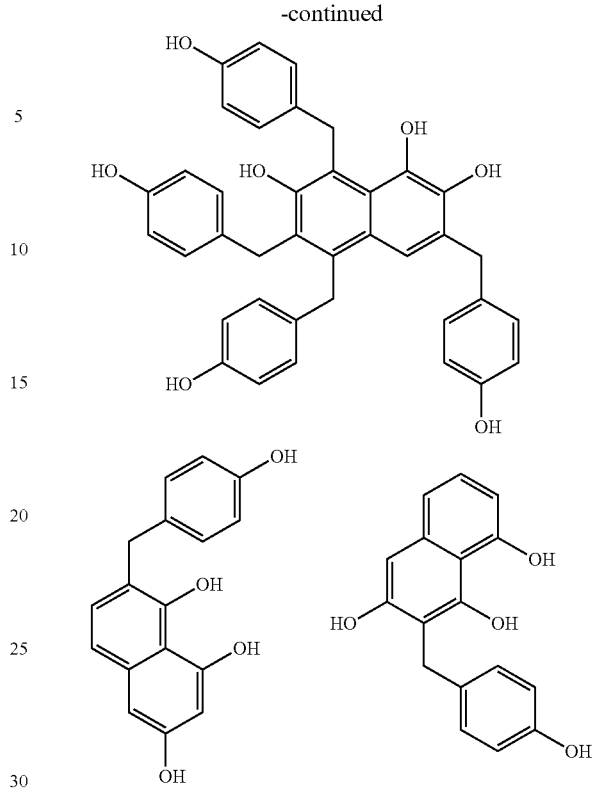
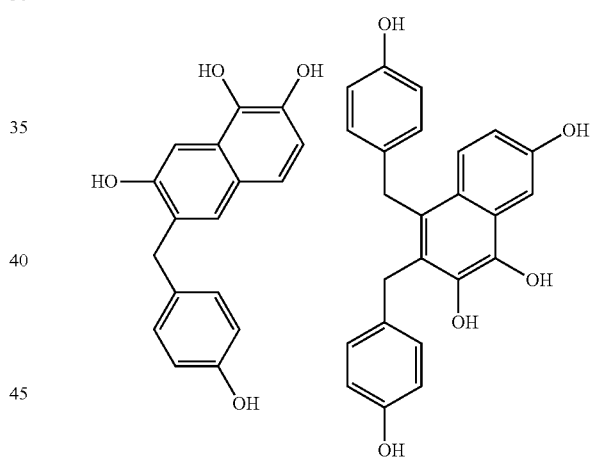
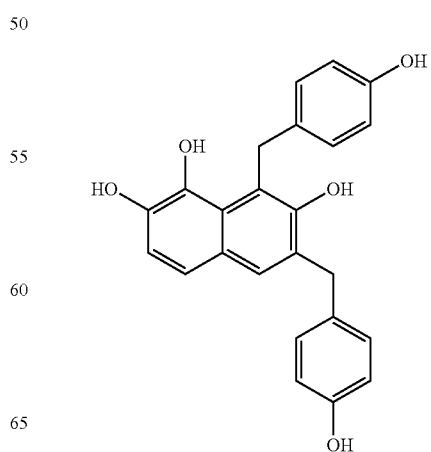

35
-continued
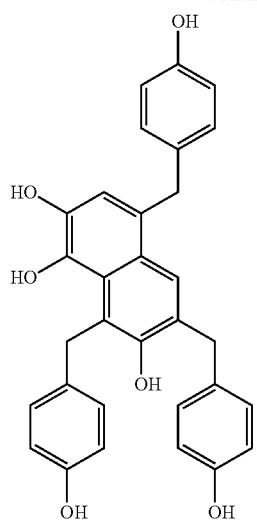
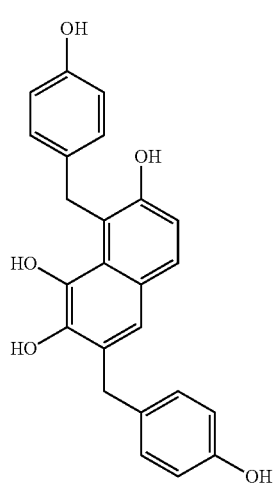
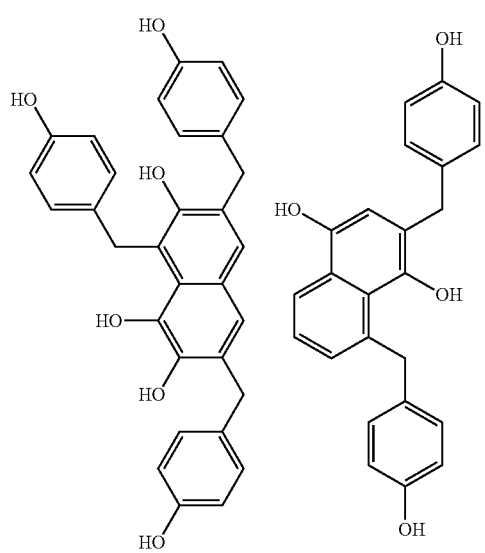
36
-continued
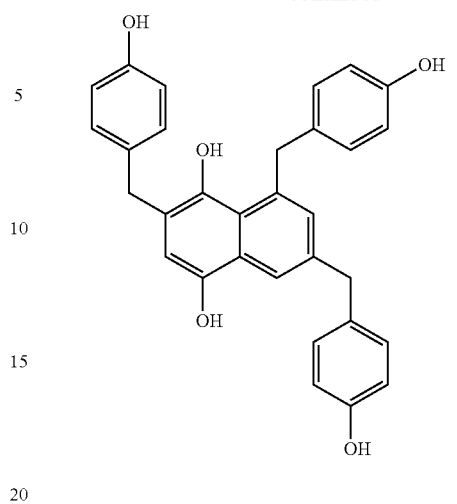
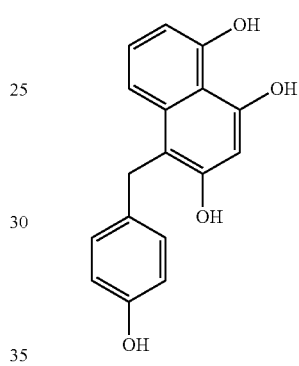
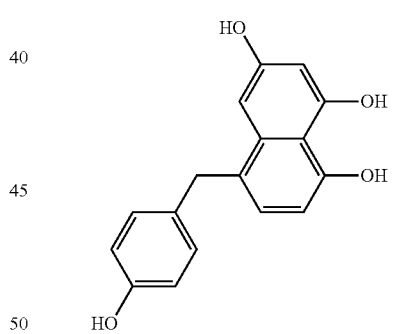

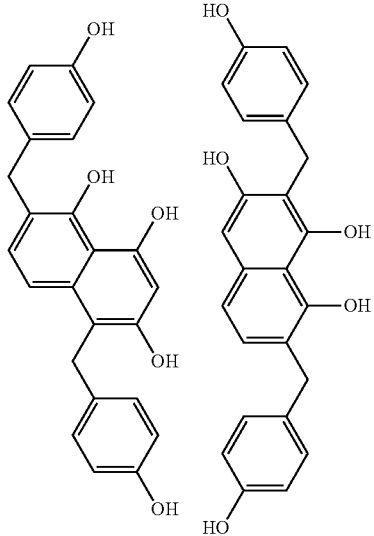
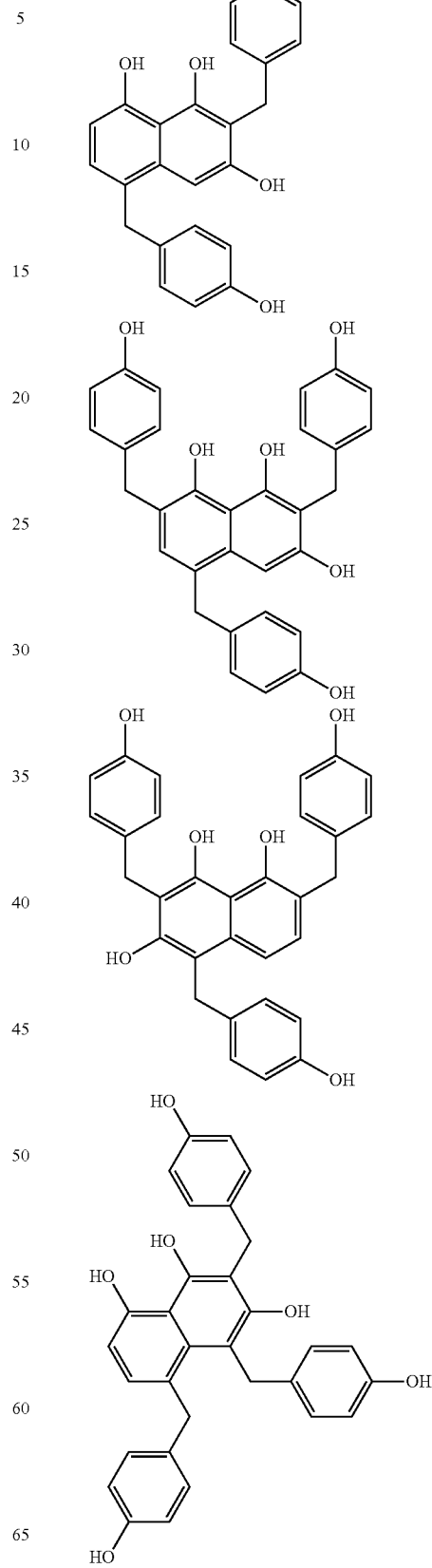

-continued
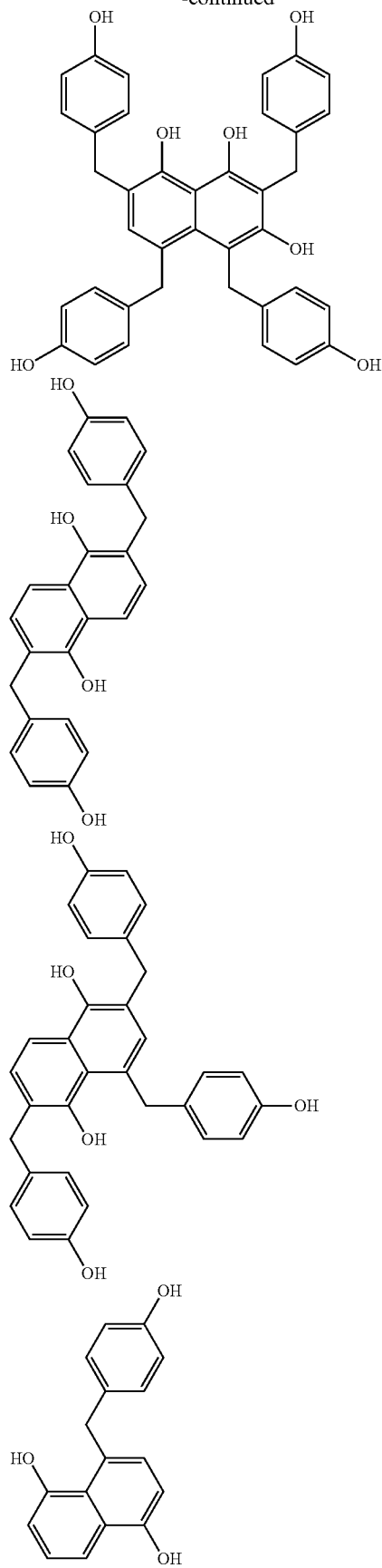
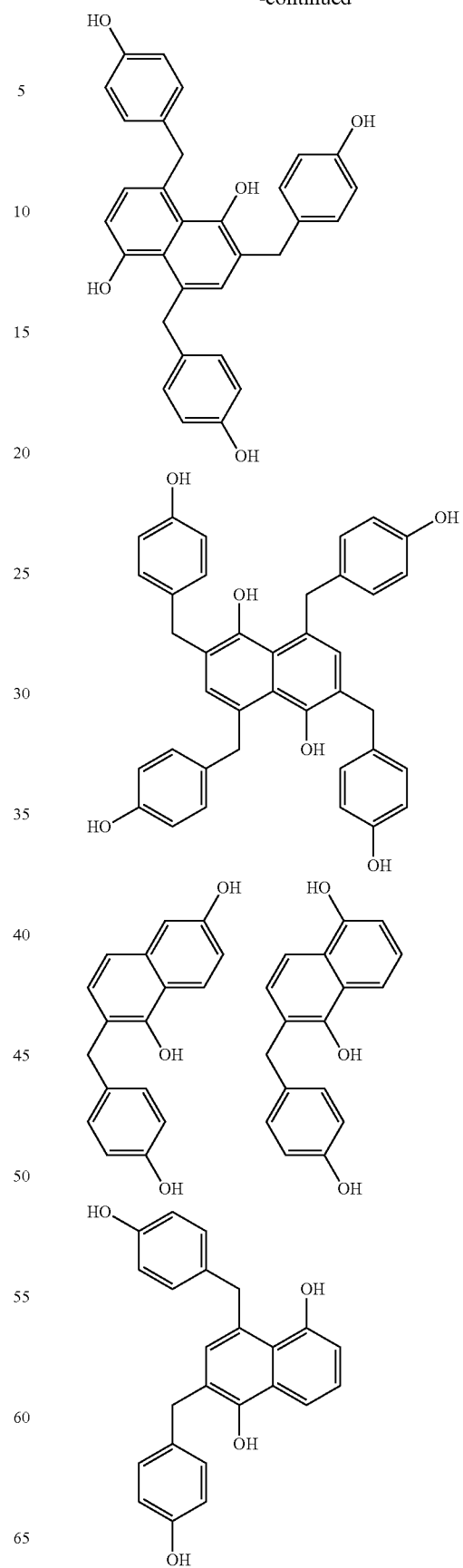

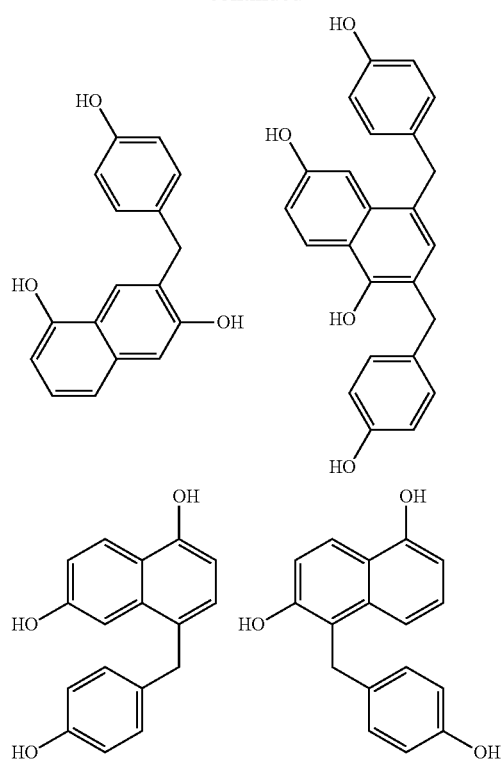
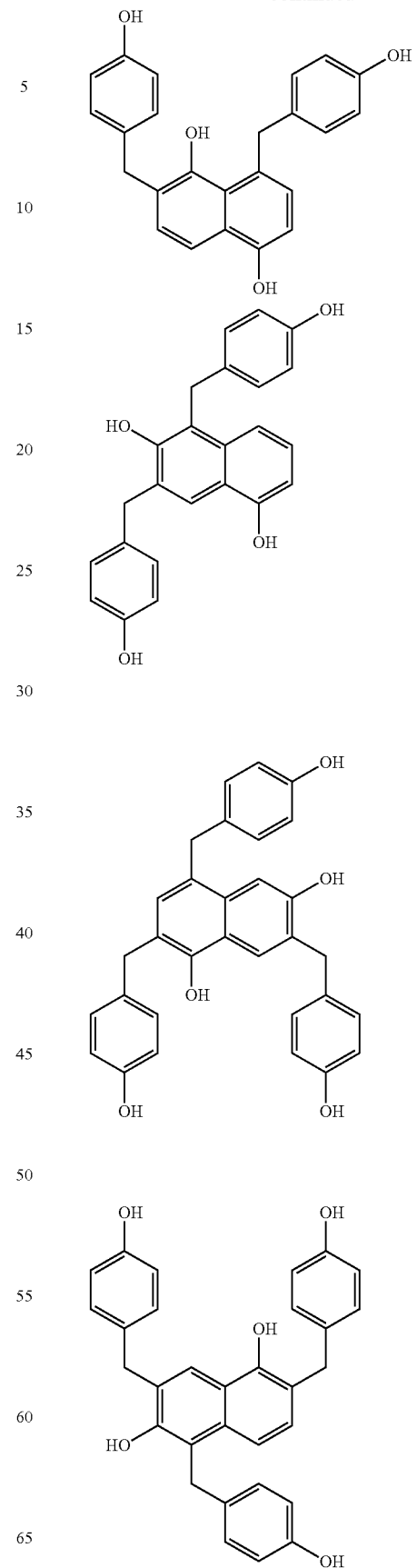

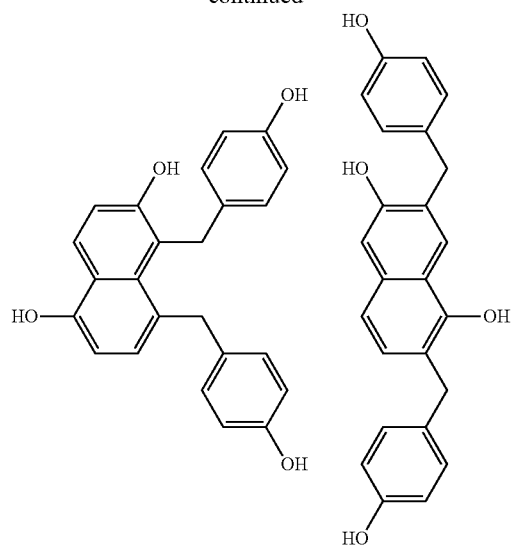
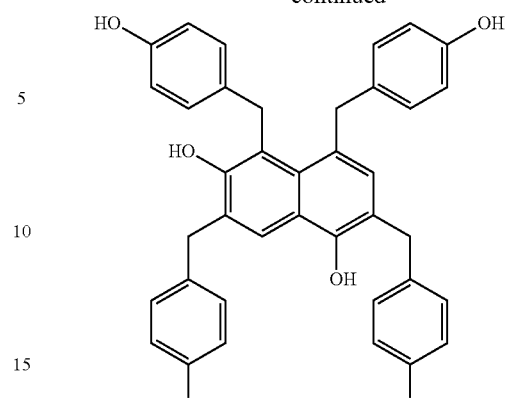
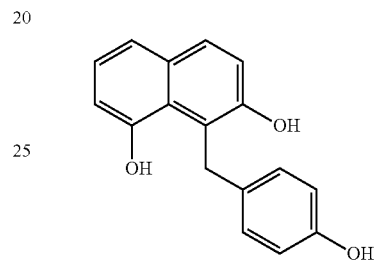
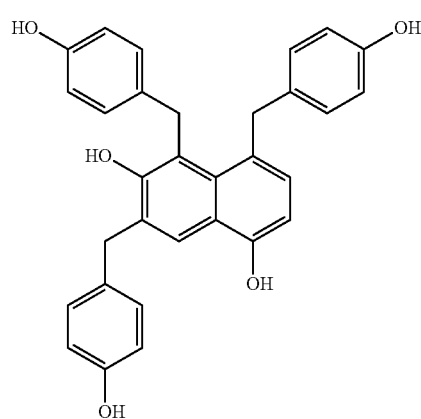
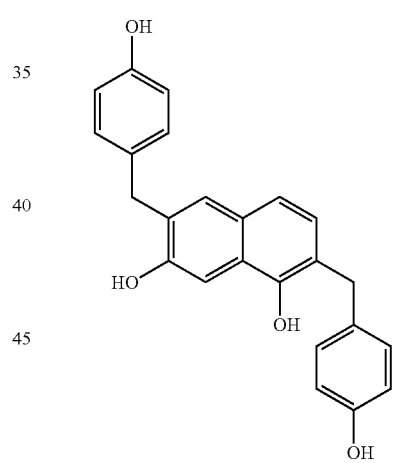
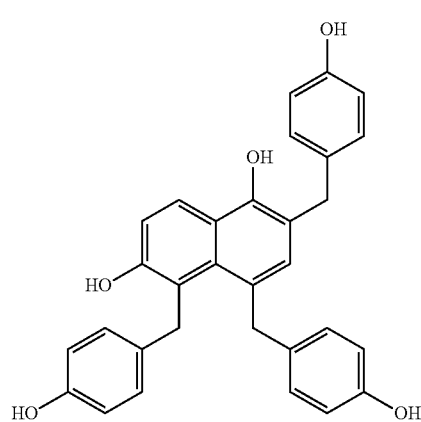
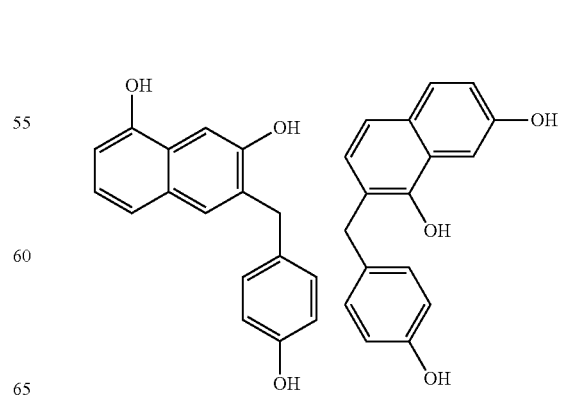

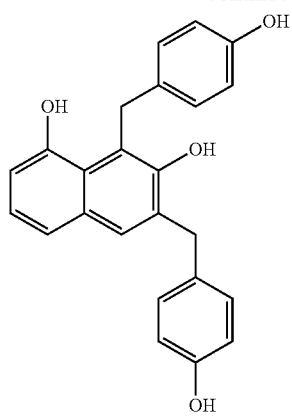
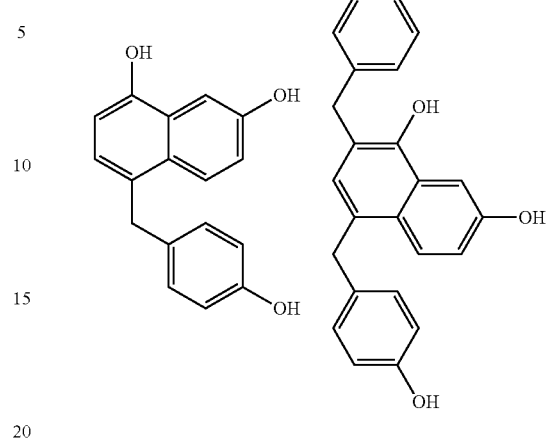
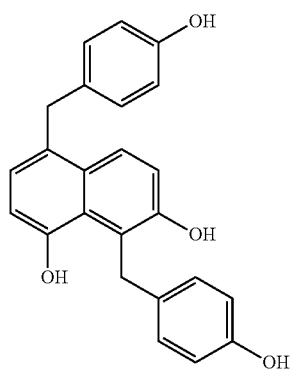
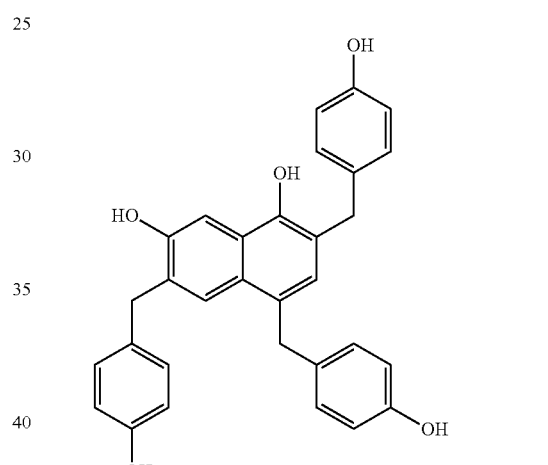
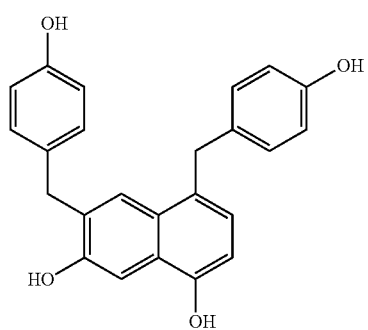
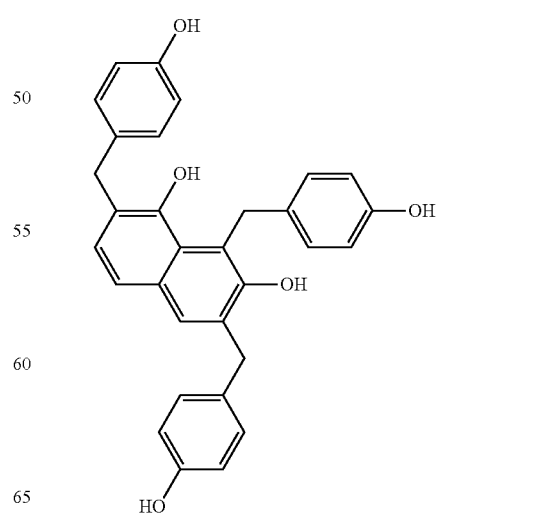
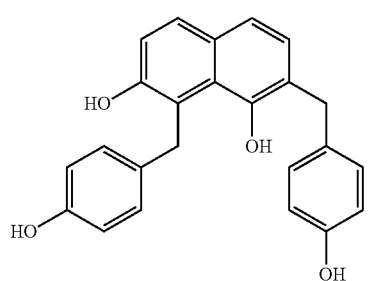

47
-continued
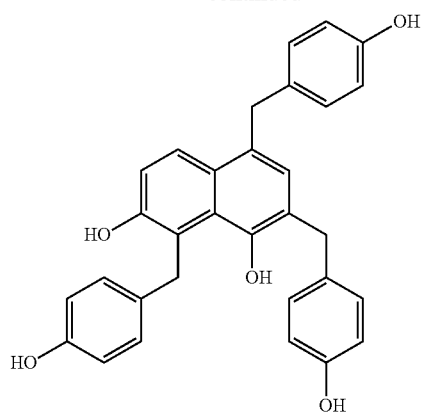
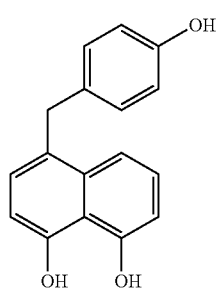
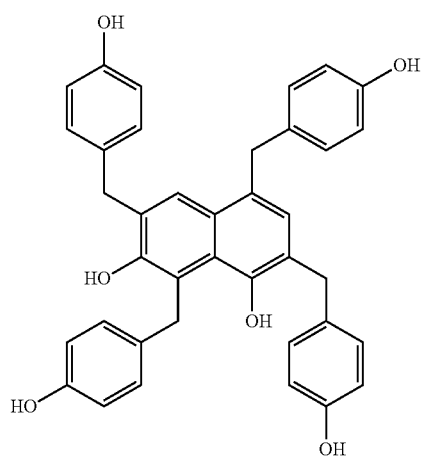
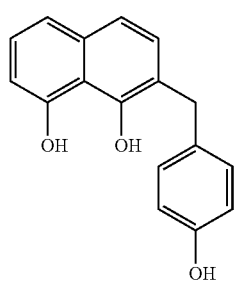
48
-continued
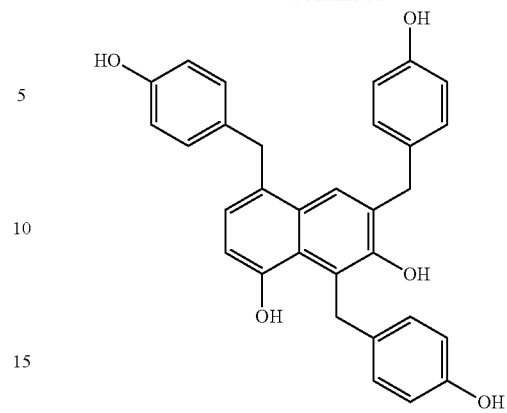
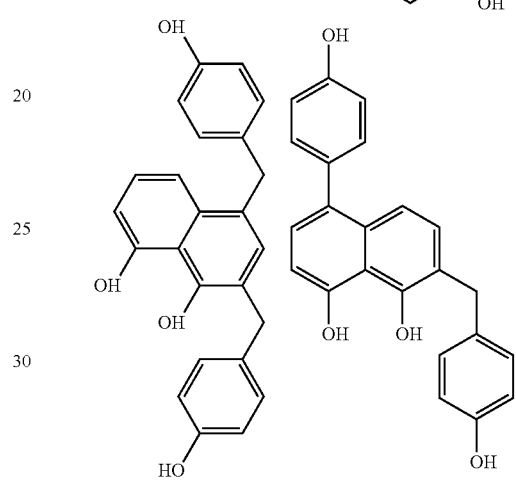
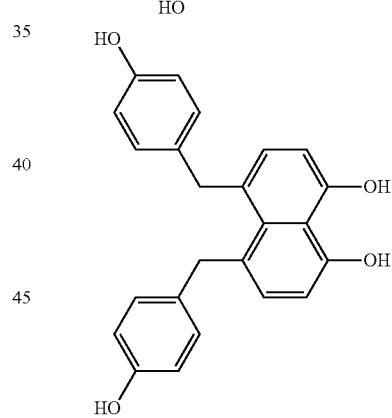
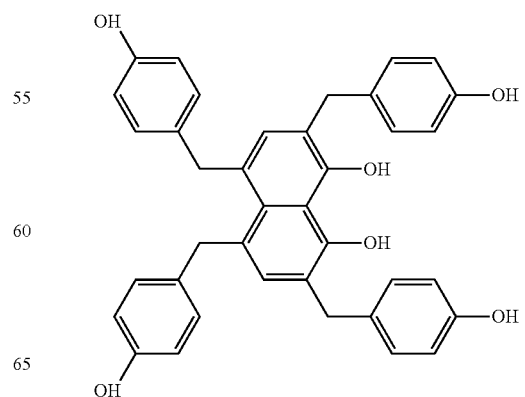

-continued
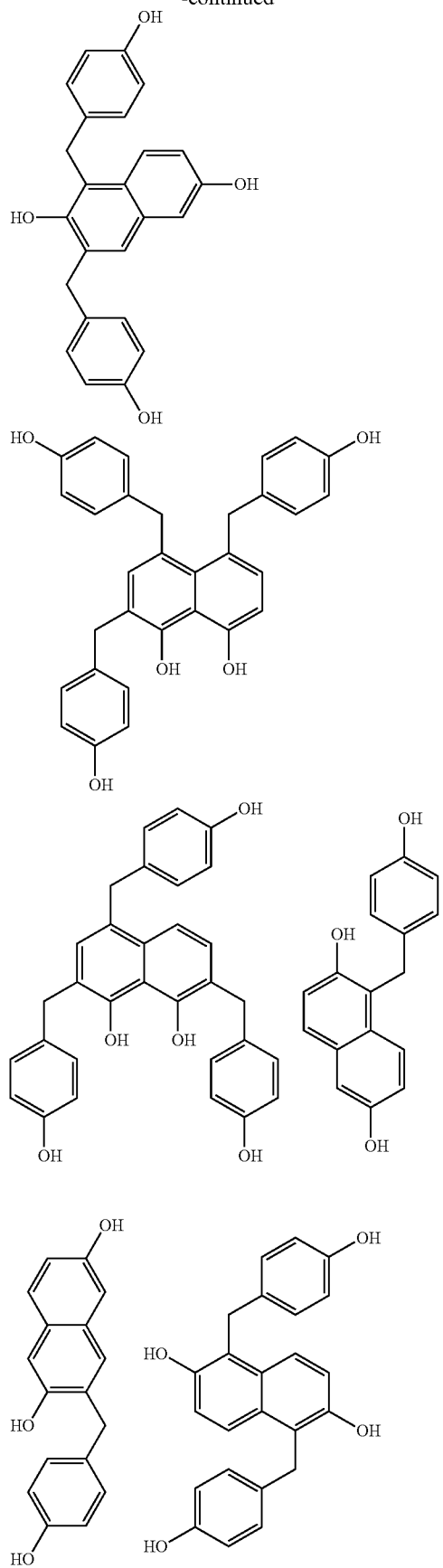
-continued
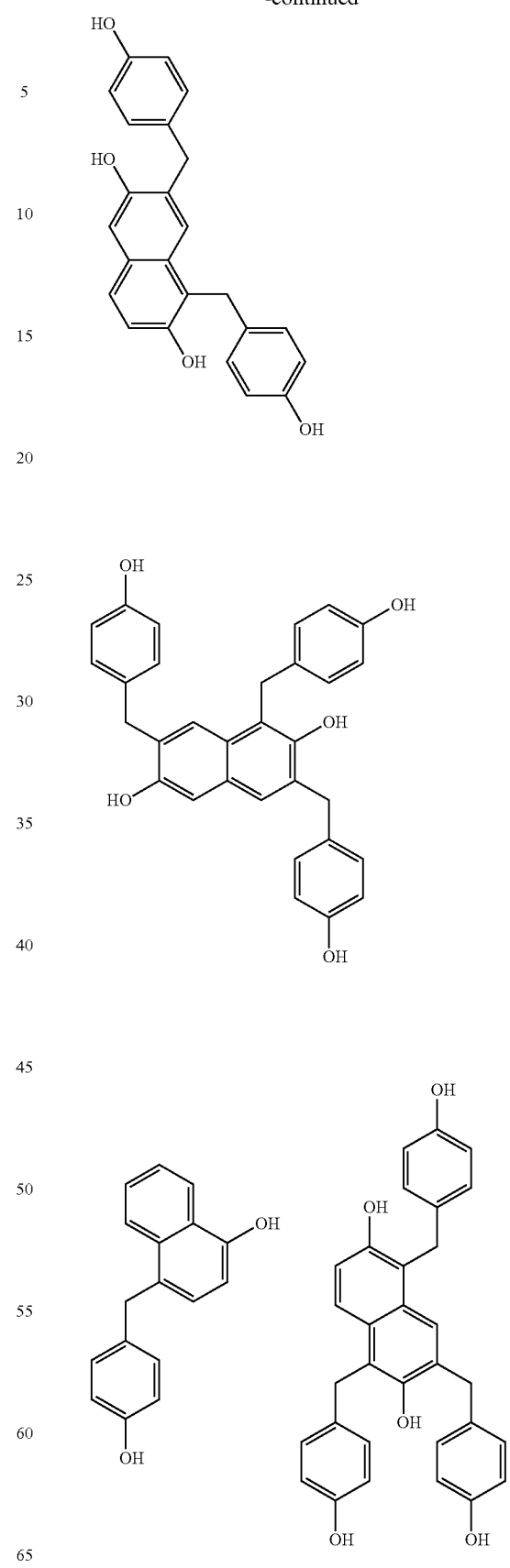

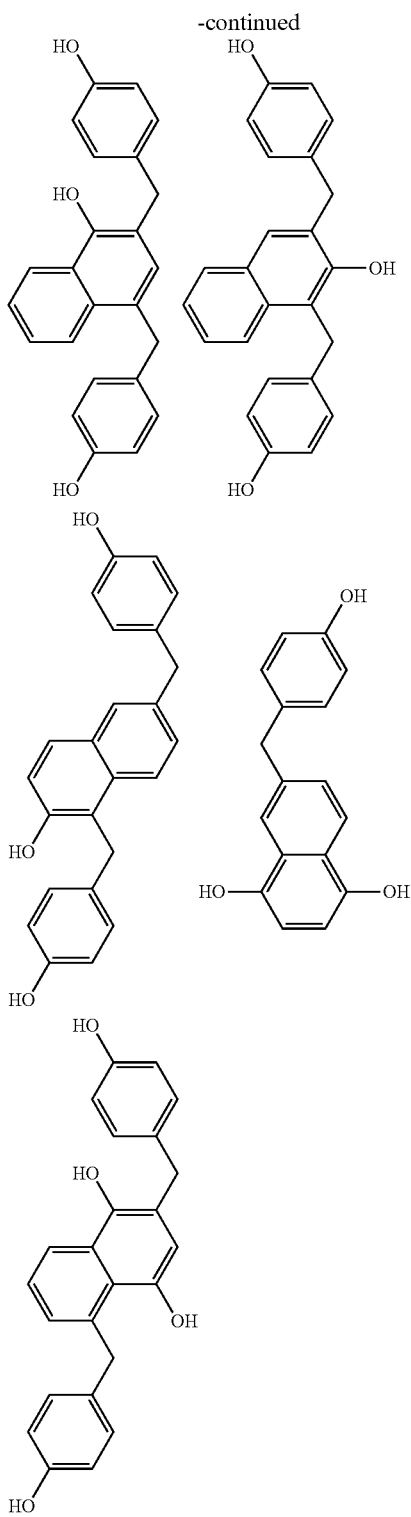

The composition containing either or both of the compound shown by the formula (2A) and the compound shown by the formula (3A) can form an organic film having better adhesiveness to not only a silicon substrate but also a structure substrate formed of silicon oxide or silicon nitride, or a hard mask composed of titanium nitride or the like. In addition, film forming property by spin coating and filling property for a stepped substrate can be improved.

Other compounds or polymers may be blended to the inventive organic film composition. The blend compound or the blend polymer is mixed with the inventive organic film compound and serves to improve the film forming property by spin coating and the filling property for a stepped substrate. The blend compound or the blend polymer is preferably a compound having a phenolic hydroxyl group. Moreover, a material having high carbon density and high etching resistance is preferable.

Examples of such a material include novolak resins of phenol, o-cresol, m-cresol, p-cresol, 2,3-dimethyl phenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, and 7-methoxy-2-naphthol, dihydroxynaphthalene such as 1,5-dihydroxynaphthalene, 1,7-dihydroxynaphthalene, and 2,6-dihydroxynaphthalene, methyl-3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, or limonene; polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and a copolymer thereof. In addition, the composition may contain a naphthol dicyclopentadiene copolymer disclosed in Japanese Patent Laid-Open Publication No. 2004-205685, a fluorene bisphenol novolak resin disclosed in Japanese Patent Laid-Open Publication No. 2005-128509, an acenaphthylene copolymer disclosed in Japanese Patent Laid-Open Publication No. 2005-250434, fullerene having a phenolic group disclosed in Japanese Patent Laid-Open Publication No. 2006-227391, a bisphenol compound and a novolak resin thereof disclosed in Japanese Patent Laid-Open Publication No. 2006-293298, a novolak resin of an adamantane phenol compound disclosed in Japanese Patent Laid-Open Publication No. 2006-285095, a bisnaphthol compound and a novolak resin thereof disclosed in Japanese Patent Laid-Open Publication No. 2010-122656, and a fullerene resin compound disclosed in Japanese Patent Laid-Open Publication No. 2008-158002. The formulation amount of the blend compound or the blend polymer is preferably 0.001 to 100 parts by mass, more preferably 0.01 to 50 parts by mass, based on 100 parts by mass of the inventive organic film compound.

The inventive organic film composition may further contain an acid generator and a crosslinking agent to promote the crosslinking reaction. The acid generator can be classified into a material that generates an acid by thermal decomposition and a material that generates an acid by light irradiation; any acid generators can be added. Illustrative examples of the acid generator include materials disclosed in paragraphs (0061) to (0085) of Japanese Patent Laid-Open Publication No. 2007-199653.

Illustrative examples of the crosslinking agent include materials disclosed in paragraphs (0055) to (0060) of Japanese Patent Laid-Open Publication No. 2007-199653.

The inventive organic film composition may further contain a surfactant to improve coating property by spin coating. Illustrative examples of the surfactant include materials disclosed in paragraphs (0142) to (0147) of Japanese Patent Laid-Open Publication No. 2009-269953.

The inventive organic film composition may further contain a basic compound to improve preservation stability. The basic compound serves as a quencher relative to an acid to prevent the crosslinking reaction from promoting by a trace of acid generated from the acid generator. Illustrative examples of the basic compound include materials disclosed in paragraphs (0086) to (0090) of Japanese Patent Laid-Open Publication No. 2007-199653.

The inventive organic film composition may further contain other additives to more greatly improve the filling and planarizing properties. The additive is not particularly limited so long as it can provide the filling and planarizing properties. Preferable example thereof include liquid additives having polyethylene glycol or polypropylene glycol structures and thermo-decomposable polymers having a weight loss ratio between 30° C. and 250° C. of 40 mass % or more and a weight average molecular weight of 300 to 200,000. The thermo-decomposable polymer preferably contains a repeating unit having an acetal structure shown by the formula (DP1) or (DP1a).

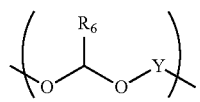

(DP1)

wherein $R_6$ represents a hydrogen atom or a saturated or unsaturated monovalent organic group having 1 to 30 carbon atoms which may be substituted; and Y represents a saturated or unsaturated divalent organic group having 2 to 30 carbon atoms.

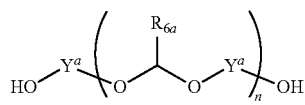

(DP1a)

wherein $R_{6a}$ represents an alkyl group having 1 to 4 carbon atoms; $Y^a$ represents a saturated or unsaturated divalent hydrocarbon group having 4 to 10 carbon atoms and optionally containing an ether bond; and "n" represents an average repeating unit number of 3 to 500.

As described above, the inventive organic film composition has good dry etching resistance, heat resistance to 400° C. or higher, and high filling and planarizing properties. Thus, the inventive organic film composition is extremely useful as a resist underlayer film material for multilayer resist processes such as a 2-layer resist process, a 3-layer resist process using a silicon-containing resist underlayer film or a silicon-containing inorganic hard mask, or a 4-layer resist using a silicon-containing resist underlayer film or a silicon-containing inorganic hard mask and an organic anti-reflective film. In addition, the inventive organic film composition, which has high filling and planarizing properties, is also useful as a planarizing material in a semiconductor apparatus manufacturing process other than the multilayer resist process.

<Method for Forming Organic Film>

The present invention provides a method for forming an organic film that functions as an organic planarizing film used in a semiconductor apparatus manufacturing process, the method comprising: applying the above-described composition for forming an organic film on a substrate to be processed by spin coating; and heating the substrate, on which the composition has been applied, at 100° C. to 600° C. for 10 to 600 seconds to form a cured film.

In this method for forming an organic film, first, the inventive organic film composition is applied on a substrate to be processed by spin coating. The spin coating method improves filling property of the composition. After spin coating, baking (heat treatment) is performed to promote the planarization by thermal flow the crosslinking reaction. This baking causes the solvent in the composition to be evaporated, thus preventing mixing with a resist upper layer film or a silicon-containing resist underlayer film formed on the organic film even when a resist upper layer film or a silicon-containing resist underlayer film is formed.

The baking is performed at 100° C. to 600° C. for 10 to 600 seconds, preferably at 200° C. to 500° C. for 10 to 300 seconds. Considering effects on device damage and wafer deformation, the upper limit of the heating temperature in a wafer process of lithography is preferably 600° C. or lower, more preferably 500° C. or lower. The heat treatment under this condition facilitates the planarization by thermal flow and the crosslinking reaction, thus enabling the formation of an organic film without mixing with an overlying film.

Furthermore, the present invention provides a method for forming an organic film that functions as an organic planarizing film used in a semiconductor apparatus manufacturing process, the method comprising: applying the above-described composition for forming an organic film on a substrate to be processed by spin coating; and heating the substrate, on which the composition has been applied, under an atmosphere having an oxygen concentration of 0.1% to 21% to form a cured film.

In this method for forming an organic film, first, the inventive organic film composition is applied on a substrate to be processed by spin coating as in the above method. After spin coating, baking (heat treatment) is performed under an atmosphere having an oxygen concentration of 0.1% to 21%. The atmosphere during baking may be any atmosphere that has an oxygen concentration of 0.1% to 21%; the atmosphere may be air or a mixed gas of an oxygen gas and an inert gas such as $N_2$, Ar, and He. The baking temperature and other conditions may be the same as above. When the baking is performed in such oxygen atmosphere, an organic film sufficiently cured can be formed.

In the inventive methods for forming an organic film, the substrate to be processed preferably has steps or a structure with a height of 30 nm or more. As described above, the inventive organic film composition has excellent filling and planarizing properties. Thus, even when the substrate to be processed has steps (level difference) or a structure with a height of 30 nm or more, a flat cured film can be formed. In other words, the inventive methods for forming an organic film are especially useful for forming a flat organic film on such a substrate to be processed.

The thickness of the organic film to be formed is appropriately selected, and is preferably 30 to 20,000 nm, particularly preferably 50 to 15,000 nm.

Moreover, the inventive methods for forming an organic film are applicable in both cases that the inventive organic film composition is used to form an organic film for a resist underlayer film or an organic film for a planarizing film.

<Patterning Process>
[3-Layer Resist Process using Silicon-Containing Resist Underlayer Film]

The present invention provides a patterning process comprising: forming an organic film on a body to be processed from the inventive composition for forming an organic film; forming a resist underlayer film on the organic film from a resist underlayer film composition containing a silicon atom; forming a resist upper layer film on the resist underlayer film from a resist upper layer film composition composed of a photoresist composition; forming a circuit pattern in the resist upper layer film; transferring the pattern to the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

The body to be processed is preferably a semiconductor apparatus substrate or the semiconductor apparatus substrate coated with any of a metal film, a metal carbide film, a metal oxide film, a metal nitride film, a metal oxycarbide film, and a metal oxynitride film. Illustrative examples thereof include a substrate made of Si, α-Si, p-Si, $SiO_2$, SiN, SiON, W, TiN, or Al, and the substrate coated with a layer to be processed, e.g. the above-described metal film, although not particularly limited thereto.

Examples of the layer to be processed include various Low-k films made of Si, $SiO_2$, SiON, SiN, p-Si, α-Si, W, W—Si, Al, Cu or Al—Si, and stopper films thereof. This layer is typically formed with a thickness of 50 to 10,000 nm, particularly 100 to 5,000 nm. In the case that the layer to be processed is formed, the substrate and the layer to be processed made of different materials are used.

The metal of the body to be processed is preferably silicon, titanium, tungsten, hafnium, zirconium, chromium, germanium, copper, silver, gold, aluminum, indium, gallium, arsenic, palladium, iron, tantalum, iridium, molybdenum, or an alloy thereof.

Additionally, the body to be processed preferably has steps or a structure with a height of 30 nm or more.

When the organic film is formed on the body to be processed from the inventive organic film composition, the inventive method for forming an organic film may be employed.

Then, a resist underlayer film (a silicon-containing resist underlayer film) is formed on the organic film from a resist underlayer film composition containing a silicon atom. The resist underlayer film composition containing a silicon atom is preferably a polysiloxane-based underlayer film composition. The silicon-containing resist underlayer film having antireflective effect can control the reflection. Although when a composition containing many aromatic groups, which provides a high etching selectivity relative to the substrate, is used as the organic film composition especially for 193-nm exposure, the k-value and thus the substrate reflection are increased, the reflection can be controlled by imparting absorption to the silicon-containing resist underlayer film so as to have an appropriate k-value. In this manner, the substrate reflection can be reduced to 0.5% or less. Preferably used as the silicon-containing resist underlayer film having antireflective effect is a polysiloxane that has a pendant anthracene for exposure of 248 nm or 157 nm, or a pendant phenyl group or a pendant light-absorbing group having a silicon-silicon bond for exposure of 193 nm, capable of crosslinking by acid or heat.

Then, a resist upper layer film is formed on the resist underlayer film from a resist upper layer film composition composed of a photoresist composition. The resist upper layer film composition may be a positive type or a negative type, and any common photoresist composition may be used. After spin coating of the resist upper layer film composition, pre-baking is preferably performed at 60 to 180° C. for 10 to 300 seconds. Thereafter, exposure, post-exposure bake (PEB), and development are carried out according to conventional methods to obtain a resist upper layer film pattern. The thickness of the resist upper layer film is preferably, but not particularly limited to, 30 to 500 nm, more preferably 50 to 400 nm.

Then, a circuit pattern (the resist upper layer film pattern) is formed in the resist upper layer film. The circuit pattern is preferably formed by a photolithography with a light source having a wavelength ranging from 10 nm to 300 nm, a direct drawing with electron beam, a nanoimprinting, or a combination thereof.

Examples of the exposure light include high energy beam having a wavelength of 300 nm or less, more specifically, deep ultraviolet ray, KrF excimer laser beam (248 nm), ArF excimer laser beam (193 nm), $F_2$ laser beam (157 nm), $Kr_2$ laser beam (146 nm), $Ar_2$ laser beam (126 nm), soft X-ray (EUV) having a wavelength of 3 to 20 nm, electron beam (EB), ion beam, and X-ray.

Additionally, the circuit pattern is preferably developed by alkaline development or development with an organic solvent.

Then, the pattern is transferred to the resist underlayer film by etching using the resist upper layer film having the formed circuit pattern as a mask. The etching of the resist underlayer film using the resist upper layer film pattern as a mask is preferably performed with a fluorocarbon gas. In this manner, a silicon-containing resist underlayer film pattern is formed.

Then, the pattern is transferred to the organic film by etching using the resist underlayer film having the transferred pattern as a mask. Since the silicon-containing resist underlayer film has resistance to etching with an oxygen gas or a hydrogen gas, the etching of the organic film using the silicon-containing resist underlayer film pattern as a mask is preferably performed with an etching gas mainly containing oxygen or hydrogen. In this manner, an organic film pattern is formed.

Then, the pattern is transferred to the body to be processed by etching using the organic film having the transferred pattern as a mask. The etching of the body to be processed (the layer to be processed) can be carried out according to a conventional method. For example, the body to be processed made of $SiO_2$, SiN, or silica low-dielectric insulating film is etched mainly with a fluorocarbon gas; the body to be processed made of p-Si, Al, or W is etched mainly with a chlorine- or bromine-based gas. When the substrate is processed by etching with a fluorocarbon gas, the silicon-containing resist underlayer film pattern is removed with processing the substrate. When the substrate is etched with a chlorine- or bromine-based gas, the silicon-containing resist underlayer film pattern needs to be removed by another dry etching with a fluorocarbon gas after processing the substrate.

The organic film obtained from the inventive organic film composition can exhibit excellent etching resistance when the body to be processed is etched as described above.

[4-Layer Resist Process using Silicon-Containing Resist Underlayer Film and Organic Antireflective Film]

Furthermore, the present invention provides a patterning process comprising: forming an organic film on a body to be processed from the inventive composition for forming an organic film; forming a resist underlayer film on the organic film from a resist underlayer film composition containing a silicon atom; forming an organic antireflective film on the resist underlayer film; forming a resist upper layer film on the organic antireflective film from a resist upper layer film composition composed of a photoresist composition; forming a circuit pattern in the resist upper layer film; transferring the pattern to the organic antireflective film and the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

This method can be performed in the same manner as the above 3-layer resist process using the silicon-containing resist underlayer film except that an organic antireflective film (BARC) is formed between the resist underlayer film and the resist upper layer film.

The organic antireflective film can be formed from a known organic antireflective film composition by spin coating.

[3-Layer Resist Process using Inorganic Hard Mask]

Furthermore, the present invention provides a patterning process comprising: forming an organic film on a body to be processed from the inventive composition for forming an organic film; forming an inorganic hard mask selected from a silicon oxide film, a silicon nitride film, and a silicon oxynitride film on the organic film; forming a resist upper layer film on the inorganic hard mask from a resist upper layer film composition composed of a photoresist composition; forming a circuit pattern in the resist upper layer film; transferring the pattern to the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

This method can be performed in the same manner as the above 3-layer resist process using the silicon-containing resist underlayer film except that an inorganic hard mask is formed on the organic film instead of the resist underlayer film.

The inorganic hard mask selected from a silicon oxide film, a silicon nitride film, and a silicon oxynitride film (a SiON film) can be formed by a CVD method or an ALD method. The method for forming the silicon nitride film is disclosed in, for example, Japanese Patent Laid-Open Publication No. 2002-334869 and International Publication No. WO2004/066377. The thickness of the inorganic hard mask is preferably 5 to 200 nm, more preferably 10 to 100 nm. The SiON film, which has a high function as an antireflective film, is most preferably used as the inorganic hard mask. Since the substrate temperature increases between 300 to 500° C. when the SiON film is formed, the underlayer film requires withstanding a temperature of 300 to 500° C. The organic film formed from the inventive organic film composition has high heat resistance and can withstand a temperature of 300 to 500° C. Thus, the organic film formed by spin coating can be combined with the inorganic hard mask formed by the CVD method or the ALD method.

[4-Layer Resist Process using Inorganic Hard Mask and Organic Antireflective Film]

Furthermore, the present invention provides a patterning process comprising: forming an organic film on a body to be processed from the inventive composition for forming an organic film; forming an inorganic hard mask selected from a silicon oxide film, a silicon nitride film, and a silicon oxynitride film on the organic film; forming an organic antireflective film on the inorganic hard mask; forming a resist upper layer film on the organic antireflective film from a resist upper layer film composition composed of a photoresist composition; forming a circuit pattern in the resist upper layer film; transferring the pattern to the organic antireflective film and the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

This method can be performed in the same manner as the above 3-layer resist process using the inorganic hard mask except that an organic antireflective film (BARC) is formed between the inorganic hard mask and the resist upper layer film.

In particular, when the SiON film is used as the inorganic hard mask, the reflection can be controlled by two antireflective films of the SiON film and the BARC film even in liquid immersion exposure at a high NA exceeding 1.0. Another merit of the BARC formation is to reduce footing of the resist upper layer film pattern, compared with a pattern just on the SiON film.

Figure 2:
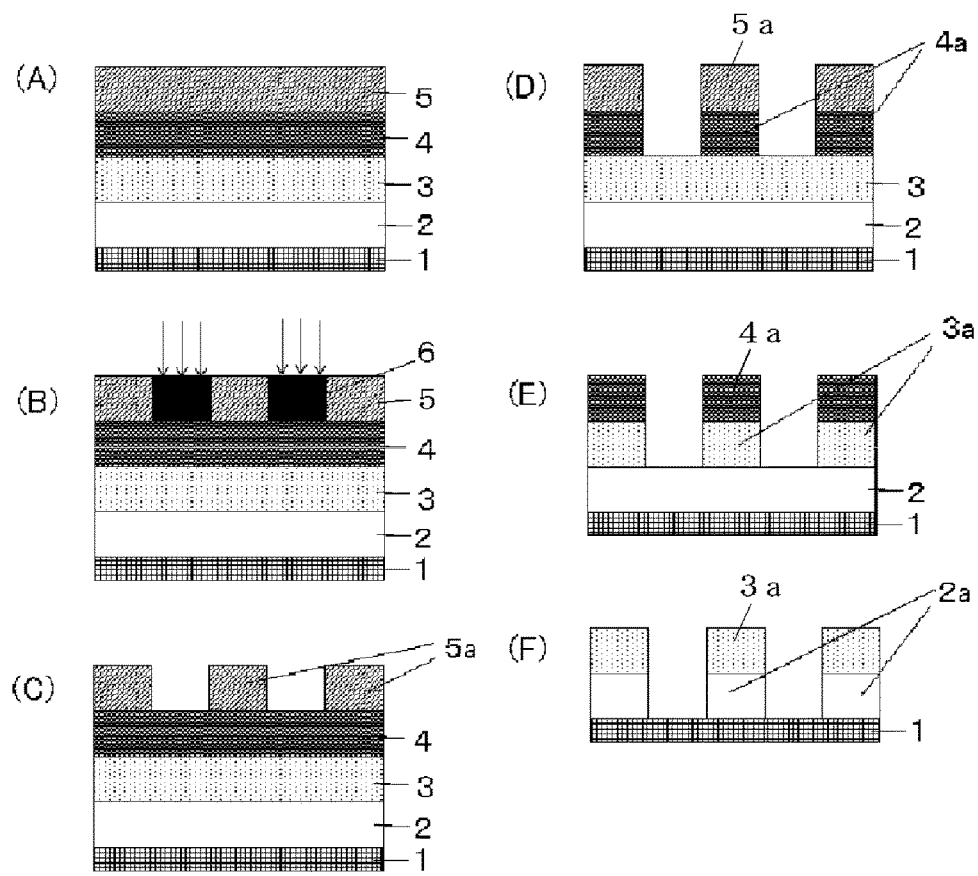
FIG. 2 is an explanatory view of an example of the inventive patterning process by the 3-layer resist process.

FIG. 2 (A) to (F) shows an example of the inventive patterning process by 3-layer resist process. In the 3-layer resist process, as shown in FIG. 2(A), after an organic film 3 is formed on a layer to be processed 2 on a substrate 1 from the inventive organic film composition, a silicon-containing resist underlayer film 4 is formed thereon, and a resist upper layer film 5 is formed thereon. Then, as shown in FIG. 2(B), an exposure portion 6 of the resist upper layer film 5 is exposed to light, followed by post exposure baking (PEB). Then, as shown in FIG. 2(C), a resist upper layer film pattern 5a is formed by development. Then, as shown in FIG. 2(D), the silicon-containing resist underlayer film 4 is processed by dry etching with a fluorocarbon gas, using the resist upper layer film pattern 5a as a mask to form a silicon-containing resist underlayer film pattern 4a. Then, as shown in FIG. 2(E), after the resist upper layer film pattern 5a is removed, the organic film 3 is etched with oxygen plasma, using the silicon-containing resist underlayer film pattern 4a as a mask to form an organic film pattern 3a. Further, as shown in FIG. 2(F), after the silicon-containing resist underlayer film pattern 4a is removed, the layer to be processed 2 is processed by etching using the organic film pattern 3a as a mask to form a pattern 2a.

In the case that the inorganic hard mask is formed, the silicon-containing resist underlayer film 4 is replaced with the inorganic hard mask. In the case that the BARC is formed, the BARC is formed between the silicon-containing resist underlayer film 4 and the resist upper layer film 5. Etching of the BARC may be carried out continuously in advance of etching of the silicon-containing resist underlayer film 4. Alternatively, after the BARC is etched alone, an etching apparatus may be changed to etch the silicon-containing resist underlayer film 4.

As described above, the inventive patterning processes can precisely form a fine pattern in the body to be processed by the multilayer resist process.

EXAMPLES

In the following, the present invention is specifically explained by referring to synthesis examples, comparative synthesis examples, examples, and comparative examples, but the present invention is not limited thereto. With respect to molecular weight and dispersity, weight average molecular weight (Mw) and number average molecular weight (Mn) were measured by gel permeation chromatography (GPC) using tetrahydrofuran as an eluent in terms of polystyrene, and dispersity (Mw/Mn) was calculated therefrom. In addition, Mw was also calculated by assuming the atomic weight of elements as follows: hydrogen=1, carbon=12, oxygen=16.

In the following synthesis examples, compounds B and compounds C shown below were used.

Compounds B: (B1) to (B9) are shown below.

(B1)

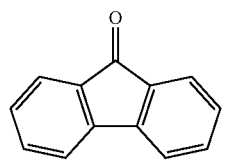

(B2)

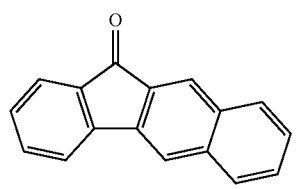

(B3)

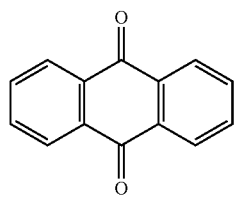

(B4)

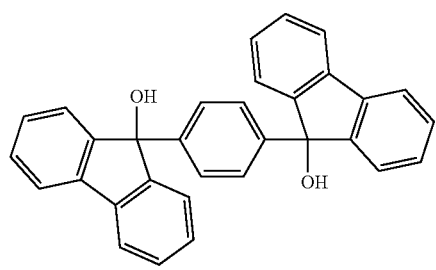

(B5)

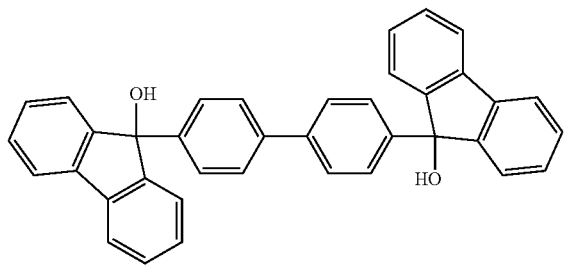

(B6)

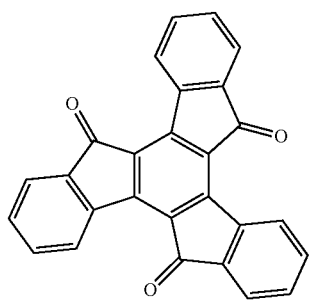

(B7)

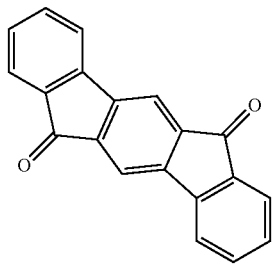

(B8)

(B9)

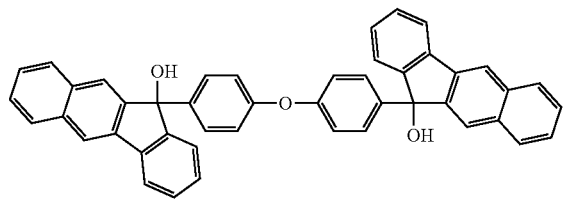

Compounds C: (C1) to (C9) are shown below.

(C1)

-continued (C2)
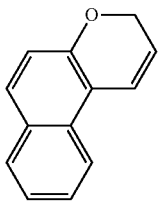

(C3)
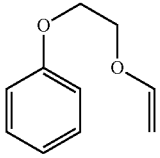

(C4)
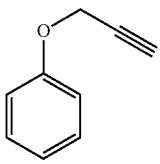

(C5)
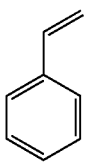

(C6)
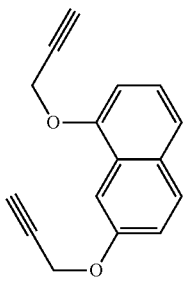

(C7)
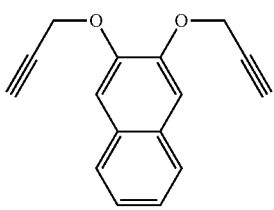

(C8)
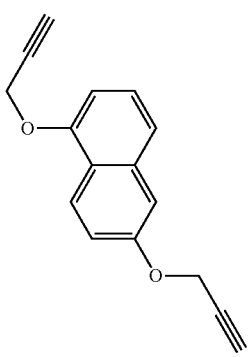

-continued (C9)
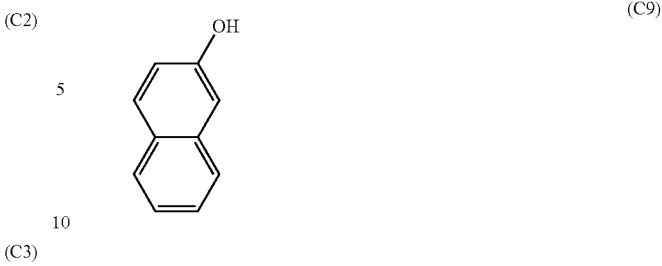

Synthesis Example 1

Synthesis of Organic Film Compound (A1)

24.8 g of the compound (B1), 75.2 g of the compound (C1), 5 mL of β-mercaptopropionic acid, and 200 mL of 1,2-dichloroethane were mixed under a nitrogen atmosphere at a liquid temperature of 60° C. to form a homogeneous solution. To the solution was gently added 10 mL of methanesulfonic acid, and the mixture was stirred at a liquid temperature of 70° C. for 12 hours. After cooling to room temperature, 400 g of methyl isobutyl ketone was added thereto, and the organic layer was washed with 1,000 g of pure water 5 times and then evaporated under reduced pressure to dryness. Then, 200 g of tetrahydrofuran (THF) was added to the residue, and a crystal was precipitated by 1,000 g of hexane. The precipitated crystal was collected by filtration with Kiriyama funnel and washed with 300 mL of hexane twice. The crystal was then collected and dried under reduced pressure at 60° C. to obtain organic film compound (A1) shown below. When the molecular weight (Mw) and dispersity (Mw/Mn) were measured by GPC, this compound had Mw of 558 and Mw/Mn of 1.01.

(A1)
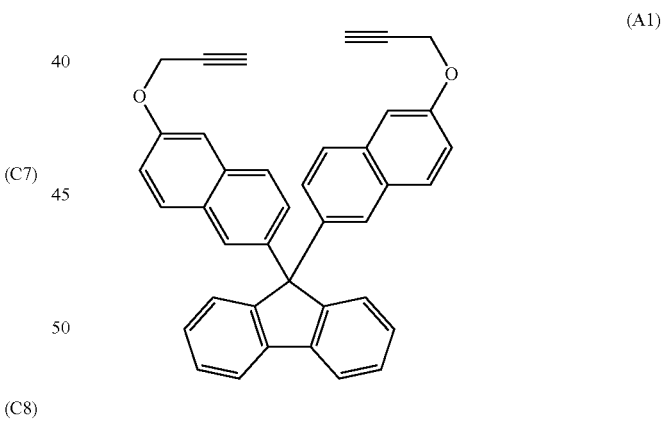

Synthesis Examples 2 to 12

Synthesis of Organic Film Compounds (A2) to (A12)

Organic film compounds (A2) to (A12) shown in Tables 1 to 3 were obtained as reaction products under the same reaction condition as in synthesis example 1 except that compounds B and compounds C shown in Tables 1 to 3 were used. The weight average molecular weight (Mw) and the dispersity (Mw/Mn) of these compounds were measured. The result is given in Table 4.

Synthesis Example 13

Synthesis of Compound (D1)

Compound (D1) shown in Table 3 was obtained as a reaction product under the same reaction condition as in synthesis example 1 except that compounds B and compounds C shown in Table 3 were used. The weight average molecular weight (Mw) and the dispersity (Mw/Mn) of the compound (D1) were measured. The result is given in Table 4.

TABLE 1

| Synthesis example | Compounds B | Compounds C | Product |
|---|---|---|---|
| 1 | (B1) 24.8 g | (C1) 75.2 g | 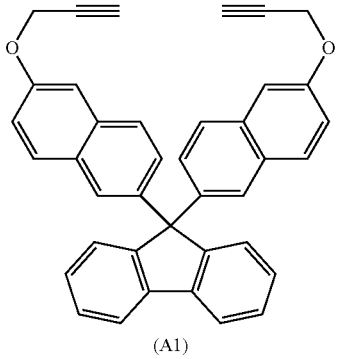 (A1) |
| 2 | (B2) 29.6 g | (C2) 70.4 g | 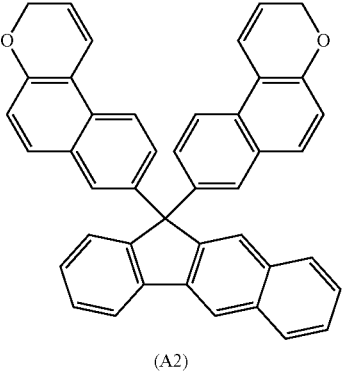 (A2) |
| 3 | (B3) 18.0 g | (C2) 82.0 g | 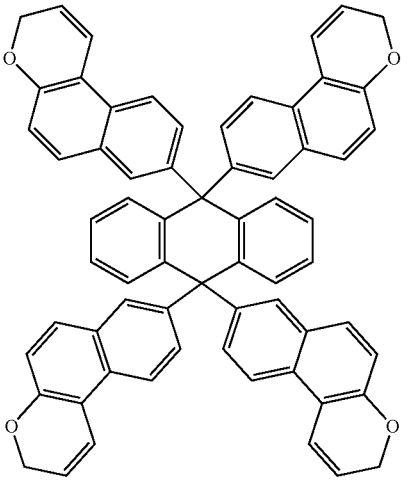 (A3) |

TABLE 1-continued
| Synthesis example | Compounds B | Compounds C | Product |
|---|---|---|---|
| 4 | (B4) 47.1 g | (C3) 52.9 g | 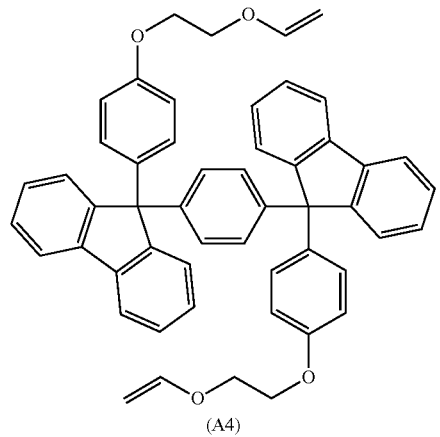 (A4) |
| 5 | (B5) 48.5 g | (C1) 51.5 g | 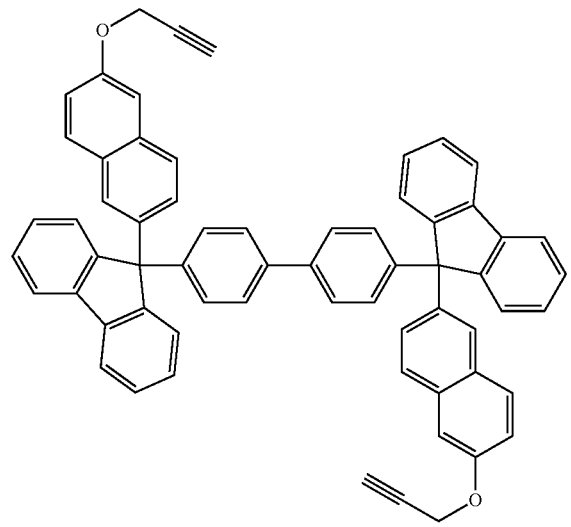 (A5) |

TABLE 2

| Synthesis example | Compounds B | Compounds C | Product |
|---|---|---|---|
| 6 | (B6) 24.4 g | (C4) 75.6 g | (A6) |
| 7 | (B7) 20.5 g | (C1) 79.5 g | (A7) |
| 8 | (B8) 36.8 g | (C5) 63.2 g | (A8) |

TABLE 2-continued
| Synthesis example | Compounds B | Compounds C | Product |
|---|---|---|---|
| 9 | (B9) 55.6 g | (C3) 44.4 g | 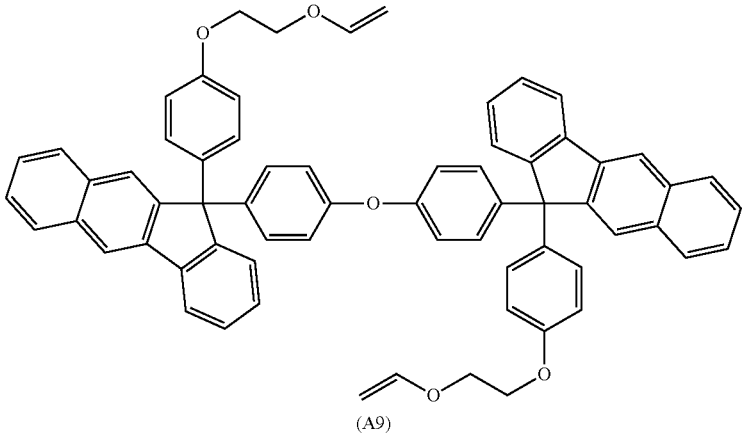 (A9) |
TABLE 3
| Synthesis example | Compounds B | Compounds C | Product |
|---|---|---|---|
| 10 | (B4) 42.1 g | (C6) 57.9 g | (A10) |
| 11 | (B5) 42.1 g | (C7) 57.9 g | (A11) |

TABLE 3-continued

| Synthesis example | Compounds B | Compounds C | Product |
|---|---|---|---|
| 12 | (B9) 42.1 g | (C8) 57.9 g | 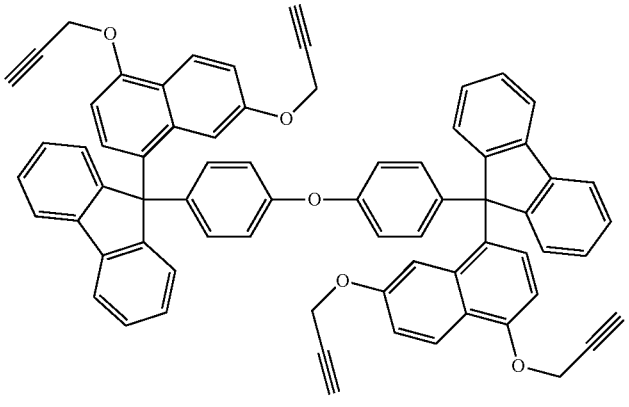<br>(A12) |
| 13 | (B5) 54.3 g | (C6) 45.7 g | 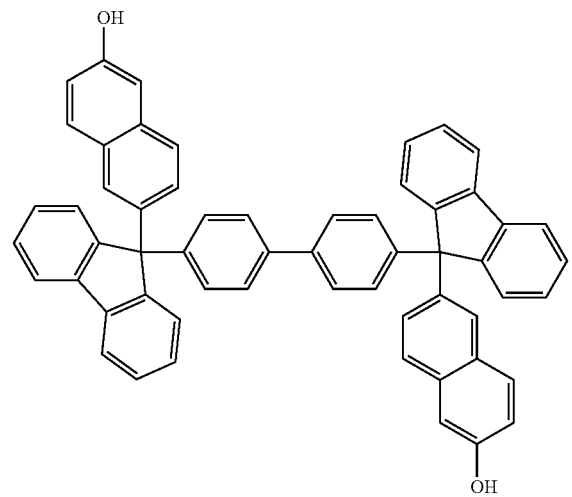<br>(D1) |

TABLE 4

| Synthesis example | Compound | Mw (calculated value) | Mw (GPC) | Mw/Mn |
|---|---|---|---|---|
| 1 | (A1) | 526 | 558 | 1.01 |
| 2 | (A2) | 576 | 622 | 1.01 |
| 3 | (A3) | 900 | 940 | 1.06 |
| 4 | (A4) | 730 | 797 | 1.01 |
| 5 | (A5) | 842 | 966 | 1.09 |
| 6 | (A6) | 1122 | 1215 | 1.08 |
| 7 | (A7) | 974 | 1042 | 1.02 |
| 8 | (A8) | 372 | 458 | 1.02 |
| 9 | (A9) | 1022 | 1111 | 1.05 |
| 10 | (A10) | 951 | 955 | 1.03 |
| 11 | (A11) | 951 | 1019 | 1.04 |
| 12 | (A12) | 951 | 1055 | 1.02 |
| 13 | (D1) | 766 | 798 | 1.07 |

Comparative Synthesis Example 1

Synthesis of Compound (R1)

72.0 g of 1-naphthol, 24.3 g of a 37% formalin solution, and 250 g of 2-methoxy-1-propanol were mixed under a nitrogen atmosphere at a liquid temperature of 80° C. to form a homogeneous solution. To the solution was gently added 18 g of a 2-methoxy-1-propanol solution containing 20% p-toluenesulfonic acid, and the mixture was stirred at a liquid temperature of 110° C. for 12 hours. After cooling to room temperature, 500 g of methyl isobutyl ketone was added thereto, and the organic layer was washed with 200 g of pure water 5 times and evaporated under reduced pressure to dryness. Then, 300 mL of THF was added to the residue, and the polymer was reprecipitated by 2,000 mL of hexane. The precipitated polymer was collected by filtration and dried under reduced pressure to obtain compound (R1). When the molecular weight (Mw) and dispersity (Mw/Mn) were measured by GPC, this compound had Mw of 1,800 and Mw/Mn of 3.33.

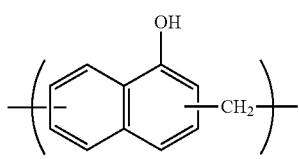

(R1)

Comparative Synthesis Example 2

Synthesis of Compound (R2)

90.1 g of 9,9-fluorenylidene-bisnaphthol, 10.5 g of a 37% formalin solution, and 270 g of 2-methoxy-1-propanol were mixed under a nitrogen atmosphere at a liquid temperature of 80° C. to form a homogeneous solution. To the solution was gently added 18 g of a 2-methoxy-1-propanol solution containing 20% p-toluenesulfonic acid, and the mixture was stirred at a liquid temperature of 110° C. for 8 hours. After cooling to room temperature, 600 g of methyl isobutyl ketone was added thereto, and the organic layer was washed with 200 g of pure water 5 times and evaporated under reduced pressure to dryness. Then, 400 mL of THF was added to the residue, and the polymer was reprecipitated by 2,000 mL of hexane. The precipitated polymer was collected by filtration and dried under reduced pressure to obtain compound (R2). When the molecular weight (Mw) and dispersity (Mw/Mn) were measured by GPC, this compound had Mw of 3,700 and Mw/Mn of 2.82.

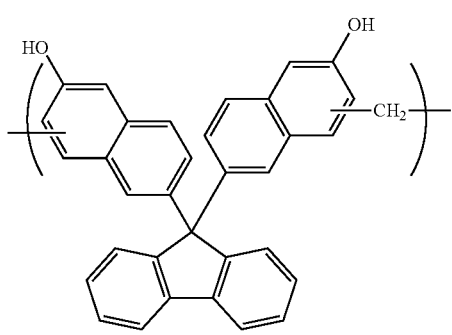

(R2)

Comparative Synthesis Example 3

Synthesis of Compound (R3)

78.8 g of 2,7-dipropargyloxynaphthalene, 21.6 g of a 37% formalin solution, and 250 g of 1,2-dichloroethane were mixed under a nitrogen atmosphere at a liquid temperature of 70° C. to form a homogeneous solution. To the solution was gently added 5 g of methanesulfonic acid, and the mixture was stirred at a liquid temperature of 80° C. for 12 hours. After cooling to room temperature, 500 g of methyl isobutyl ketone was added thereto, and the organic layer was washed with 200 g of pure water 5 times and evaporated under reduced pressure to dryness. Then, 300 mL of THF was added to the residue, and the polymer was reprecipitated by 2,000 mL of hexane. The precipitated polymer was collected by filtration and dried under reduced pressure to obtain compound (R3). When the molecular weight (Mw) and dispersity (Mw/Mn) were measured by GPC, this compound had Mw of 2,700 and Mw/Mn of 1.54.

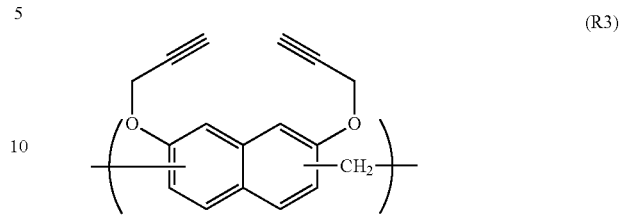

(R3)

[Preparation of Organic Film Composition (UDL-1 to 22)]

The organic film compounds (A1) to (A12) and the compounds (D1), (R1) to (R3), as additives, crosslinking agents (CR1), (CR2), and (CR3) and acid generator (AG1), and as a high-boiling point solvent, (S1) 1,6-diacetoxy-hexane (boiling point: 260° C.) or (S2) tripropylene glycol monomethyl ether (boiling point: 242° C.) were dissolved in a solvent containing propylene glycol monomethyl ether acetate (PGMEA) and 0.1 mass % FC-4430 (available from Sumitomo 3M Ltd.) with the proportion shown in Table 5. The solution was filtered through a 0.1-μm filter made of a fluorinated resin to prepare organic film compositions (UDL-1 to 22). UDL-1 to 17 containing the inventive organic film compounds (A1) to (A12) correspond to the inventive organic film compositions, while UDL-18 to 22 containing the compounds (R1) to (R3) synthesized in comparative synthesis examples correspond to comparative organic film compositions.

TABLE 5

| Organic film composition | Compound 1 (part by mass) | Compound 2 (part by mass) | Compound 3 (part by mass) | PGMEA (part by mass) | High-boiling point solvent (part by mass) |
|---|---|---|---|---|---|
| UDL-1 | A1(10) | — | — | 90 | — |
| UDL-2 | A2(10) | — | — | 90 | — |
| UDL-3 | A3(10) | — | — | 90 | — |
| UDL-4 | A4(10) | — | — | 90 | — |
| UDL-5 | A5(10) | — | — | 90 | — |
| UDL-6 | A6(10) | — | — | 90 | — |
| UDL-7 | A7(10) | — | — | 90 | — |
| UDL-8 | A8(10) | — | — | 90 | — |
| UDL-9 | A9(10) | — | — | 90 | — |
| UDL-10 | A10(10) | — | — | 90 | — |
| UDL-11 | A11(10) | — | — | 90 | — |
| UDL-12 | A12(10) | — | — | 90 | — |
| UDL-13 | A1(9) | D1(1) | — | 90 | — |
| UDL-14 | A1(9) | CR1(1) | — | 90 | — |
| UDL-15 | A1(8) | A5(1) | CR2(1) | 90 | — |
| UDL-16 | A5(10) | — | — | 80 | S1(10) |
| UDL-17 | A7(10) | — | — | 80 | S2(10) |
| UDL-18 | R1(10) | — | — | 90 | — |
| UDL-19 | R2(10) | — | — | 90 | — |
| UDL-20 | R3(10) | — | — | 90 | — |
| UDL-21 | R1(10) | CR1(2) | AG1(0.5) | 90 | — |
| UDL-22 | R2(10) | CR3(2) | AG1(0.5) | 90 | — |

The crosslinking agents (CR1), (CR2), and (CR3) and acid generator (AG1) are shown below.

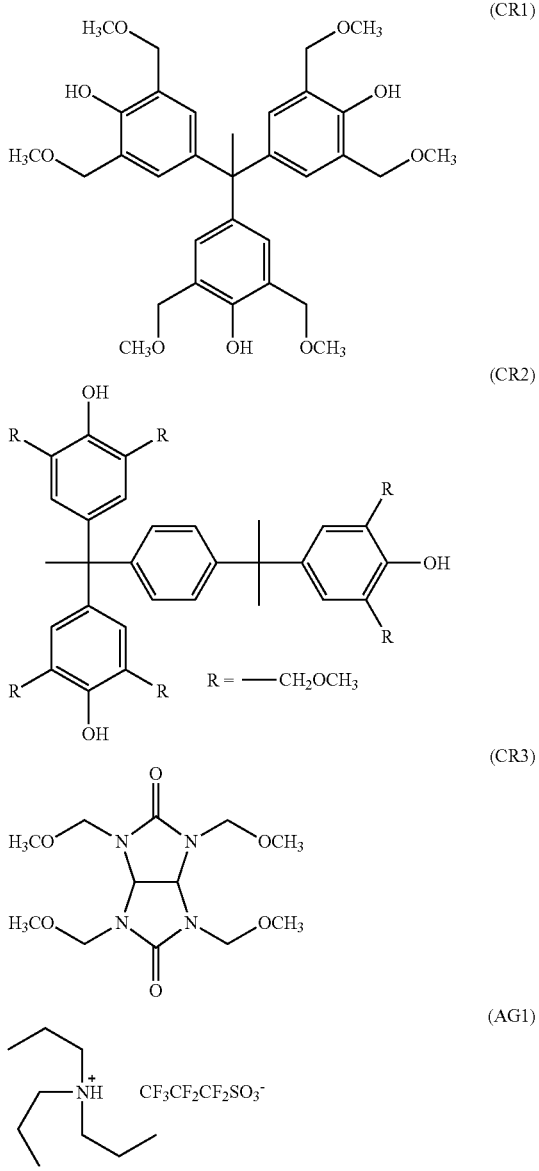

Filling Property Evaluation

Examples 1-1 to 1-17 and Comparative Examples 1-1 to 1-5

Figure 3:
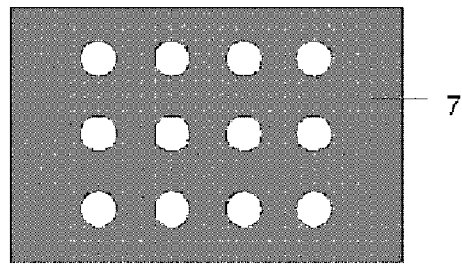
FIG. 3 is an explanatory view of a method for evaluating the filling property in examples.
Figure 3:
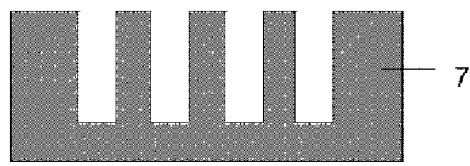
Figure 3:
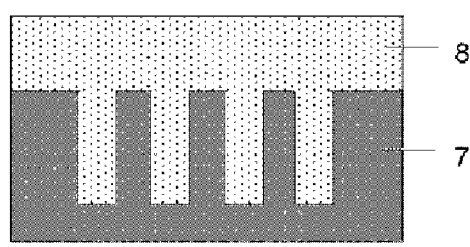

The organic film compositions (UDL-1 to 22) were each applied on a SiO$_2$ wafer substrate having a dense hole pattern (hole diameter: 0.16 μm, hole depth: 0.50 μm, distance between the centers of adjacent two holes: 0.32 μm) and baked with a hot plate at 250° C. and 450° C. for 60 seconds to form an organic film. The substrate used is a base substrate 7 (SiO$_2$ wafer substrate) having a dense hole pattern as shown in FIG. 3(G) (downward view) and FIG. 3(H) (sectional view). Cross-sectional shapes of the obtained wafer substrates were observed by a scanning electron microscope (SEM), and whether the holes were filled with the organic film without voids or not was checked. The result is given in Table 6. When an organic film composition having poor filling property is used, voids occur inside the holes in this evaluation. When an organic film composition having good filling property is used, the holes of the base substrate 7 having the dense hole pattern are filled with the organic film 8 without voids in this evaluation, as shown in FIG. 3(I).

TABLE 6

| | Organic film composition | presence/absence of voids | |
|---|---|---|---|
| | | Baking at 250° C. | Baking at 450° C. |
| Example 1-1 | UDL-1 | absence | absence |
| Example 1-2 | UDL-2 | absence | absence |
| Example 1-3 | UDL-3 | absence | absence |
| Example 1-4 | UDL-4 | absence | absence |
| Example 1-5 | UDL-5 | absence | absence |
| Example 1-6 | UDL-6 | absence | absence |
| Example 1-7 | UDL-7 | absence | absence |
| Example 1-8 | UDL-8 | absence | absence |
| Example 1-9 | UDL-9 | absence | absence |
| Example 1-10 | UDL-10 | absence | absence |
| Example 1-11 | UDL-11 | absence | absence |
| Example 1-12 | UDL-12 | absence | absence |
| Example 1-13 | UDL-13 | absence | absence |
| Example 1-14 | UDL-14 | absence | absence |
| Example 1-15 | UDL-15 | absence | absence |
| Example 1-16 | UDL-16 | absence | absence |
| Example 1-17 | UDL-17 | absence | absence |
| Comparative example 1-1 | UDL-18 | presence | presence |
| Comparative example 1-2 | UDL-19 | presence | presence |
| Comparative example 1-3 | UDL-20 | presence | presence |
| Comparative example 1-4 | UDL-21 | presence | presence |
| Comparative example 1-5 | UDL-22 | presence | presence |

Table 6 indicates that examples 1-1 to 1-17 using the inventive organic film compositions (UDL-1 to 17) could fill the hole pattern without voids regardless of the baking temperature and thus had good filling property. On the other hand, comparative examples 1-1 to 1-5 using the comparative organic film compositions (UDL-18 to 22) caused voids at both the baking temperatures and thus had poor filling property.

Planarizing Property Evaluation

Examples 2-1 to 2-17 and Comparative Examples 2-1 to 2-5

Figure 4:
FIG. 4 is an explanatory view of a method for evaluating the planarizing property in examples.
Figure 4:
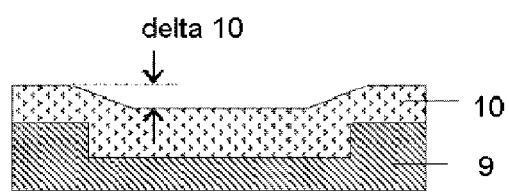

The organic film compositions (UDL-1 to 22) were each applied on a base substrate 9 (a SiO$_2$ wafer substrate) having a giant isolated trench pattern (FIG. 4(J), trench width: 10 μm, trench depth: 0.10 μm), and baked under conditions shown in Table 7. Then, a step between the trench portion and the non-trench portion of the organic film 10 (delta 10 in FIG. 4(K)) was observed by an atomic force microscope (AFM) NX10 manufactured by Park systems Corp. The result is given in Table 7. In this evaluation, the smaller the step, the better the planarizing property. Moreover, in this evaluation, the trench pattern having 0.10-μm depth was generally planarized by forming the organic film having about 0.2-μm thickness from the organic film composition. This evaluation condition is special and severe to measure the planarizing property.

TABLE 7

| | Organic film composition | Step (nm) | Baking condition |
|---|---|---|---|
| Example 2-1 | UDL-1 | 30 | 450° C. × 60 sec |
| Example 2-2 | UDL-2 | 25 | 450° C. × 60 sec |
| Example 2-3 | UDL-3 | 30 | 450° C. × 60 sec |
| Example 2-4 | UDL-4 | 30 | 450° C. × 60 sec |
| Example 2-5 | UDL-5 | 35 | 450° C. × 60 sec |
| Example 2-6 | UDL-6 | 25 | 450° C. × 60 sec |
| Example 2-7 | UDL-7 | 35 | 450° C. × 60 sec |
| Example 2-8 | UDL-8 | 45 | 450° C. × 60 sec |
| Example 2-9 | UDL-9 | 30 | 450° C. × 60 sec |
| Example 2-10 | UDL-10 | 30 | 450° C. × 60 sec |
| Example 2-11 | UDL-11 | 35 | 450° C. × 60 sec |
| Example 2-12 | UDL-12 | 30 | 450° C. × 60 sec |
| Example 2-13 | UDL-13 | 30 | 450° C. × 60 sec |
| Example 2-14 | UDL-14 | 35 | 450° C. × 60 sec |
| Example 2-15 | UDL-15 | 30 | 450° C. × 60 sec |
| Example 2-16 | UDL-16 | 25 | 450° C. × 60 sec |
| Example 2-17 | UDL-17 | 25 | 450° C. × 60 sec |
| Comparative example 2-1 | UDL-18 | 115 | 450° C. × 60 sec |
| Comparative example 2-2 | UDL-19 | 105 | 450° C. × 60 sec |
| Comparative example 2-3 | UDL-20 | 110 | 450° C. × 60 sec |
| Comparative example 2-4 | UDL-21 | 100 | 450° C. × 60 sec |
| Comparative example 2-5 | UDL-22 | 115 | 450° C. × 60 sec |

Table 7 indicates that examples 2-1 to 2-17 using the inventive organic film compositions (UDL-1 to 17) had a smaller step between the trench portion and the non-trench portion of the organic film and thus had more excellent planarizing property than comparative examples 2-1 to 2-5 using the comparative organic film compositions (UDL-18 to 22). Moreover, examples 2-16 and 2-17, in which the high-boiling point solvent was added to the inventive organic film compound, improved the planarizing property by addition of the high-boiling point solvent, and thus the effect of the high-boiling point solvent could be observed.

Heat Resistance Evaluation

Examples 3-1 to 3-15 and Comparative Examples 3-1 to 3-5

The organic film compositions (UDL-1 to 15, UDL-18 to 22) were each applied on a silicon substrate and baked at 250° C. to form an organic film having a thickness of about 300 nm, and film thickness T1 after baking at 250° C. was measured. The substrate was then further baked at 450° C., and film thickness T2 after baking at 450° C. was measured. From the measurement results, film loss rate expressed by T2/T1 was calculated. The result is given in Table 8.

TABLE 8

| | Organic film composition | Film thickness T1 after baking at 250° C. [nm] | Film thickness T2 after baking at 450° C. [nm] | Film loss rate [%] (T2/T1) |
|---|---|---|---|---|
| Example 3-1 | UDL-1 | 301.5 | 300.6 | 99.7 |
| Example 3-2 | UDL-2 | 300.7 | 295.6 | 98.3 |
| Example 3-3 | UDL-3 | 292.3 | 290.9 | 99.5 |
| Example 3-4 | UDL-4 | 309.2 | 307.2 | 99.4 |
| Example 3-5 | UDL-5 | 304.2 | 299.9 | 98.6 |
| Example 3-6 | UDL-6 | 304.4 | 301.6 | 99.1 |
| Example 3-7 | UDL-7 | 308.5 | 305.0 | 98.9 |
| Example 3-8 | UDL-8 | 303.1 | 300.1 | 99.0 |
| Example 3-9 | UDL-9 | 295.1 | 290.8 | 98.6 |
| Example 3-10 | UDL-10 | 299.8 | 294.4 | 98.2 |
| Example 3-11 | UDL-11 | 303.6 | 301.2 | 99.2 |
| Example 3-12 | UDL-12 | 305.7 | 299.6 | 98.0 |
| Example 3-13 | UDL-13 | 314.8 | 308.7 | 98.0 |
| Example 3-14 | UDL-14 | 307.2 | 302.2 | 98.4 |
| Example 3-15 | UDL-15 | 298.9 | 291.6 | 98.3 |
| Comparative example 3-1 | UDL-18 | 311.7 | 263.3 | 84.5 |
| Comparative example 3-2 | UDL-19 | 304.7 | 302.0 | 99.1 |
| Comparative example 3-3 | UDL-20 | 303.5 | 248.7 | 81.9 |
| Comparative example 3-4 | UDL-21 | 297.1 | 247.6 | 83.3 |
| Comparative example 3-5 | UDL-22 | 301.9 | 301.8 | 99.9 |

As shown in Table 8, the film thickness was less reduced after baking at 450° C. in examples 3-1 to 3-15 using the inventive organic film compositions (UDL-1 to 15), which indicates that the inventive compositions had heat resistance to 400° C. or higher. On the other hand, comparative examples 3-1, 3-3, and 3-4 using the comparative organic film compositions (UDL-18, 20, and 21) resulted in a large reduction in film thickness after baking at 450° C. and thus had worse heat resistance than examples 3-1 to 3-15. Comparative examples 3-2 and 3-5 using the comparative organic film compositions (UDL-19 and 22), which contain the compound (R2), i.e., fluorene bisphenol novolak resin excellent in heat resistance, had good heat resistance.

Patterning Test in Flat Substrate

Examples 4-1 to 4-15 and Comparative Examples 4-1 to 4-5

The organic film compositions (UDL-1 to 15, UDL-18 to 22) were each applied on a flat silicon wafer substrate on which a 300-nm $SiO_2$ film has been formed, and then baked at 450° C. for 60 seconds to form an organic film. A CVD-SiON hard mask was formed thereon, and an organic antireflective film composition (ARC-29A, available from Nissan Chemical Industries, Ltd.) was applied thereon and baked at 210° C. for 60 seconds to form an organic antireflective film having a thickness of 80 nm. An ArF monolayer resist was applied thereon as a resist upper layer film composition and baked at 105° C. for 60 seconds to form a photoresist film having a thickness of 100 nm. A liquid immersion top coat composition (TC-1) was applied on the photoresist film and baked at 90° C. for 60 seconds to form a top coat having a thickness of 50 nm.

The resist upper layer film composition (the ArF monolayer resist) was prepared by dissolving polymer (RP1), acid generator (PAG1), and basic compound (Amine1) in a solvent containing 0.1 mass % FC-430 (available from Sumitomo 3M Ltd.) with the proportion shown in Table 9 and filtering the solution through a 0.1-μm filter made of a fluorinated resin.

TABLE 9

| | Polymer (part by mass) | Acid generator (part by mass) | Basic compound (part by mass) | Solvent (part by mass) |
|---|---|---|---|---|
| ArF monolayer resist | RP1 (100) | PAG1 (6.6) | Amine1 (0.8) | PGMEA (2500) |

The polymer (RP1), acid generator (PAG1), and basic compound (Amine1) are shown below.

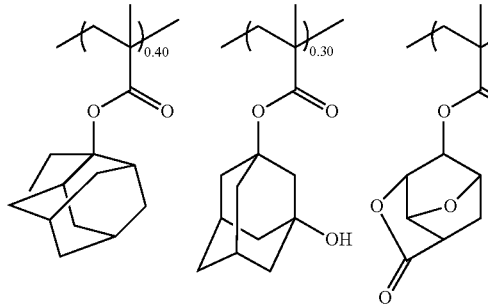

Mw7,800

RP1

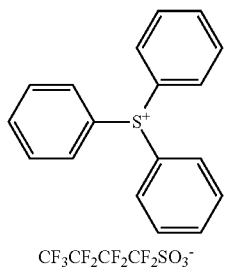

CF$_3$CF$_2$CF$_2$CF$_2$SO$_3^-$

PAG1

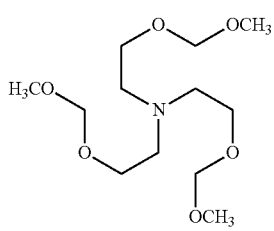

Amine1

The liquid immersion top coat composition (TC-1) was prepared by dissolving polymer (PP1) in an organic solvent with the proportion shown in Table 10 and filtering the solution through a 0.1-μm filter made of a fluorinated resin.

TABLE 10

| | Polymer (part by mass) | Organic solvent (part by mass) |
|---|---|---|
| TC-1 | PP1 (100) | Diisoamyl ether (2700) 2-methyl-1-butanol (270) |

The polymer (PP1) is shown below.

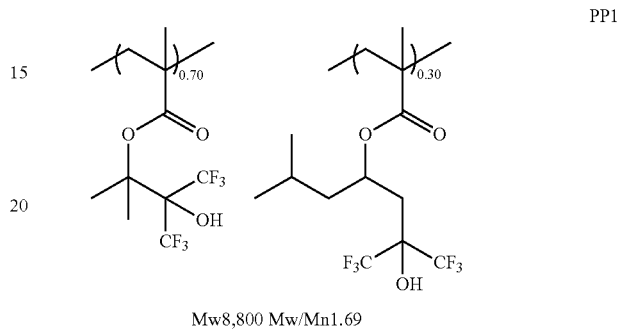

Mw8,800 Mw/Mn1.69

Then, the substrate was exposed with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds to obtain a 55 nm 1:1 positive line and space pattern (a resist upper layer film pattern).

Then, the organic antireflective film and the CVD-SiON hard mask were processed by dry etching using the resist upper layer film pattern as a mask (pattern transfer) with an etching apparatus Telius manufactured by Tokyo Electron Ltd., to form a hard mask pattern, the organic film was processed by dry etching using the obtained hard mask pattern as a mask (pattern transfer) to form an organic film pattern, and the SiO$_2$ film was processed by dry etching using the obtained organic film pattern as a mask (pattern transfer). The etching conditions are as follows.

(Condition for Transferring the Resist Upper Layer Film Pattern to the SiON Hard Mask)

| Chamber pressure | 10.0 Pa |
|---|---|
| RF power | 1,500 W |
| CF$_4$ gas flow rate | 75 mL/min |
| O$_2$ gas flow rate | 15 mL/min |
| Time | 15 sec |

(Condition for Transferring the Hard Mask Pattern to the Organic Film)

| Chamber pressure | 2.0 Pa |
|---|---|
| RF power | 500 W |
| Ar gas flow rate | 75 mL/min |
| O$_2$ gas flow rate | 45 mL/min |
| Time | 120 sec |

(Condition for Transferring the Organic Film Pattern to the SiO$_2$ Film)

| | |
|---|---|
| Chamber pressure | 2.0 Pa |
| RF power | 2,200 W |
| C$_5$F$_{12}$ gas flow rate | 20 mL/min |
| C$_2$F$_6$ gas flow rate | 10 mL/min |
| Ar gas flow rate | 300 mL/min |
| O$_2$ gas flow rate | 60 mL/min |
| Time | 90 sec |

Cross-section of the obtained pattern was observed with an electron microscope (S-4700) manufactured by Hitachi, Ltd. The result is given in Table 11.

TABLE 11

| | Organic film composition | Pattern profile after etching for transferring to substrate |
|---|---|---|
| Example 4-1 | UDL-1 | vertical profile |
| Example 4-2 | UDL-2 | vertical profile |
| Example 4-3 | UDL-3 | vertical profile |
| Example 4-4 | UDL-4 | vertical profile |
| Example 4-5 | UDL-5 | vertical profile |
| Example 4-6 | UDL-6 | vertical profile |
| Example 4-7 | UDL-7 | vertical profile |
| Example 4-8 | UDL-8 | vertical profile |
| Example 4-9 | UDL-9 | vertical profile |
| Example 4-10 | UDL-10 | vertical profile |
| Example 4-11 | UDL-11 | vertical profile |
| Example 4-12 | UDL-12 | vertical profile |
| Example 4-13 | UDL-13 | vertical profile |
| Example 4-14 | UDL-14 | vertical profile |
| Example 4-15 | UDL-15 | vertical profile |
| Comparative example 4-1 | UDL-18 | pattern collapse |
| Comparative example 4-2 | UDL-19 | vertical profile |
| Comparative example 4-3 | UDL-20 | pattern collapse |
| Comparative example 4-4 | UDL-21 | pattern collapse |
| Comparative example 4-5 | UDL-22 | vertical profile |

As shown in Table 11, all examples 4-1 to 4-15, which used the inventive organic film compositions (UDL-1 to 15), could finally transfer the resist upper layer film pattern to the silicon wafer substrate (the SiO$_2$ film) well. This result demonstrates that the inventive organic film composition is useful for fine processing by the multilayer resist method. On the other hand, comparative examples 4-1, 4-3, and 4-4, which used the comparative organic film compositions (UDL-18, 20, and 21) having insufficient heat resistance, caused pattern collapse at patterning, and a good pattern could not be finally obtained. Comparative examples 4-2 and 4-5, which used the comparative organic film compositions (UDL-19 and 22) had good heat resistance as described above and thus succeeded in patterning in the flat substrate without problems.

Patterning Test in Substrate having Trench Pattern

Examples 5-1 to 5-15 and Comparative Examples 5-1 to 5-5

Except that the organic film compositions (UDL-1 to 15, UDL-18 to 22) were each applied on a SiO$_2$ wafer substrate having a trench pattern (trench width: 10 trench depth: 0.10 μm) and baked at 450° C. for 60 seconds to form an organic film, a CVD-SiON hard mask, an organic antireflective film, a photoresist film, and a top coat were successively formed, the exposure, development, and dry etching were performed to transfer the pattern to the SiO$_2$ wafer substrate, in the same manner as in the patterning test in the flat substrate. The cross-sectional shape of the obtained pattern was then observed. The result is given in Table 12.

TABLE 12

| | Organic film composition | Pattern profile after etching for transferring to substrate |
|---|---|---|
| Example 5-1 | UDL-1 | vertical profile |
| Example 5-2 | UDL-2 | vertical profile |
| Example 5-3 | UDL-3 | vertical profile |
| Example 5-4 | UDL-4 | vertical profile |
| Example 5-5 | UDL-5 | vertical profile |
| Example 5-6 | UDL-6 | vertical profile |
| Example 5-7 | UDL-7 | vertical profile |
| Example 5-8 | UDL-8 | vertical profile |
| Example 5-9 | UDL-9 | vertical profile |
| Example 5-10 | UDL-10 | vertical profile |
| Example 5-11 | UDL-11 | vertical profile |
| Example 5-12 | UDL-12 | vertical profile |
| Example 5-13 | UDL-13 | vertical profile |
| Example 5-14 | UDL-14 | vertical profile |
| Example 5-15 | UDL-15 | vertical profile |
| Comparative example 5-1 | UDL-18 | pattern collapse |
| Comparative example 5-2 | UDL-19 | pattern collapse |
| Comparative example 5-3 | UDL-20 | pattern collapse |
| Comparative example 5-4 | UDL-21 | pattern collapse |
| Comparative example 5-5 | UDL-22 | pattern collapse |

As shown in Table 12, all examples 5-1 to 5-15, which used the inventive organic film compositions (UDL-1 to 15), could finally transfer the resist upper layer film pattern to the SiO$_2$ wafer substrate well. This result demonstrates that the inventive organic film composition is also useful for fine processing by the multilayer resist method even with a substrate having a trench pattern. On the other hand, comparative examples 5-1, 5-3, and 5-4, which used the comparative organic film compositions (UDL-18, 20, and 21), not only had insufficient heat resistance, but also failed in filling a pattern. Thus, these comparative examples caused pattern collapse at patterning, and a good pattern could not be finally obtained. Comparative examples 5-2 and 5-5, which used the comparative organic film compositions (UDL-19 and 22), had heat resistance but failed in filling a pattern. Thus, these comparative examples caused pattern collapse at patterning in the substrate having a trench pattern, and a good pattern could not be finally obtained.

The above results revealed the following. The inventive organic film composition containing the inventive organic film compound has good dry etching resistance, heat resistance to 400° C. or higher, and high filling and planarizing properties. Thus, this composition is extremely useful as an organic film composition for multilayer resist process. In addition, the inventive patterning processes using this composition can precisely form a fine pattern even in a body to be processed having steps.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A compound for forming an organic film shown by the formula (1A),
$$R\text{--}(\text{--}X)_{m1} \quad (1A)$$
wherein m1 is 2, 4 or 6; and formula (1A) is at least one selected from the following compounds:
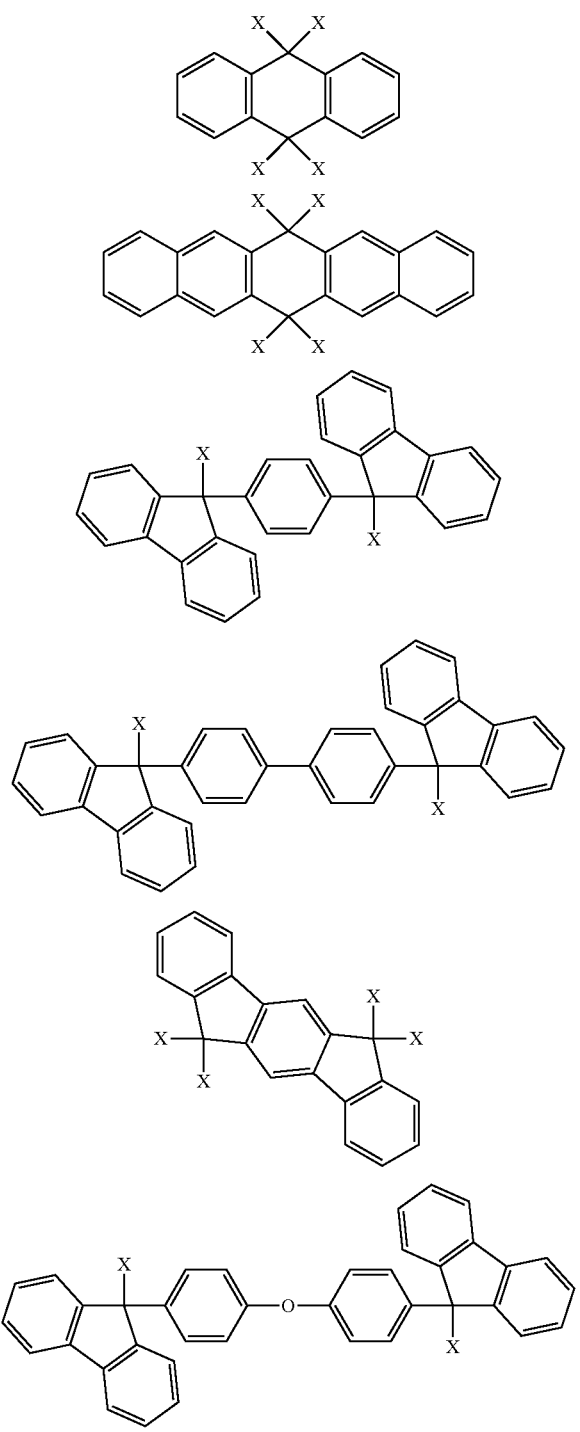
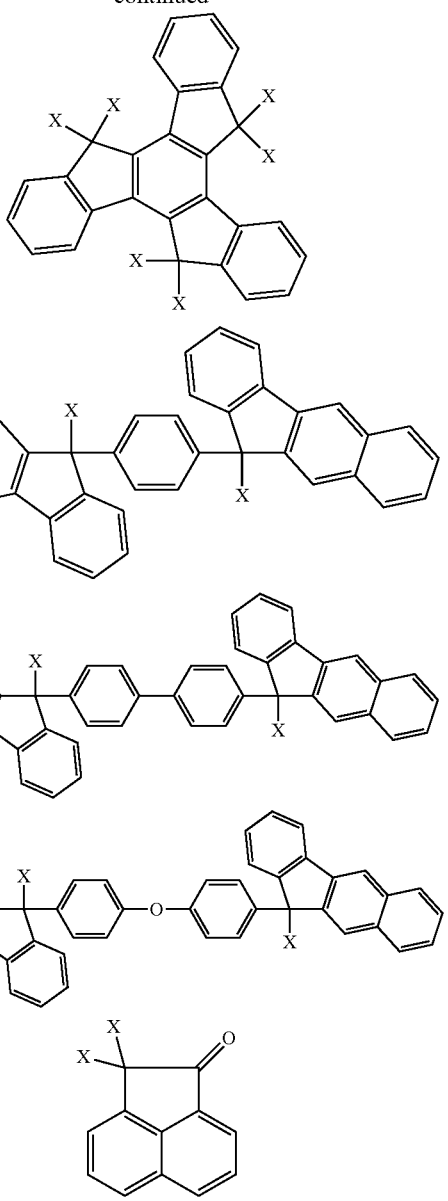
wherein X represents a group shown by at least one selected from the following structures represented by formula (1B):
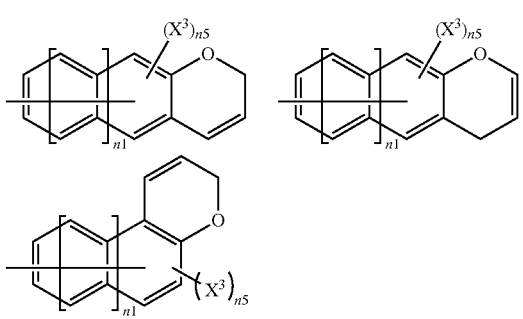
(1B)

-continued

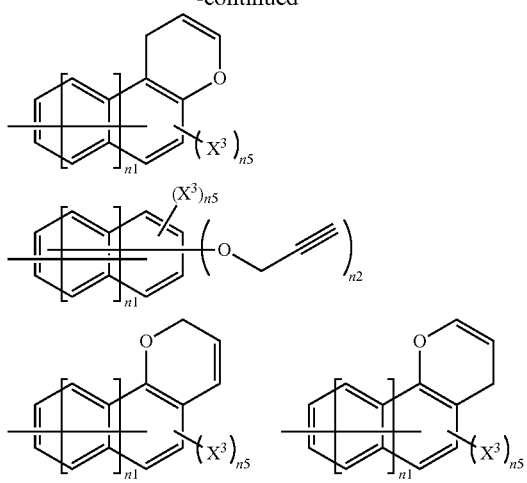

wherein n1 represents 1; n2 represents 1 or 2; $X^3$ represents a group shown by the formula (1C); and n5 represents 0, 1, or 2,

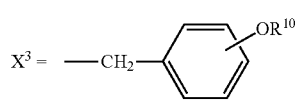

wherein $R^{10}$ represents a hydrogen atom or a saturated or unsaturated hydrocarbon group having 1 to 10 carbon atoms, in which a hydrogen atom of the benzene ring in the formula (1C) may be substituted with a methyl group or a methoxy group, and
wherein the compound satisfies $1.00 \leq Mw/Mn \leq 1.25$ where Mw is a weight average molecular weight and Mn is a number average molecular weight measured by gel permeation chromatography in terms of polystyrene.

2. The compound for forming an organic film according to claim 1, wherein the compound has a molecular weight of 2,500 or less, the molecular weight being calculated on the basis of the formula (1A).

3. A composition for forming an organic film, comprising the compound according to claim 1 and an organic solvent.

4. The composition for forming an organic film according to claim 3, further comprising either or both of a compound shown by the formula (2A) and a compound shown by the formula (3A), $$R{+}X'{)}_{m2} \quad (2A)$$

wherein R represents a single bond or an organic group having 1 to 50 carbon atoms; X' represents a group shown by the formula (2B); and m2 represents an integer satisfying $1 \leq m2 \leq 5$,

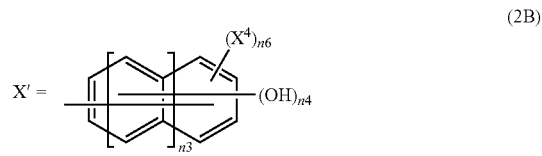

wherein n3 represents 0 or 1; n4 represents 1 or 2; $X^4$ represents a group shown by the formula (2C); and n6 represents 0, 1, or 2,

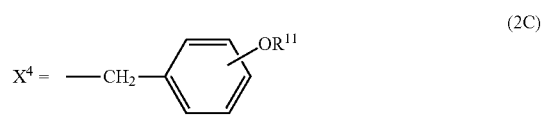

wherein $R^{11}$ represents a hydrogen atom or a saturated or unsaturated hydrocarbon group having 1 to 10 carbon atoms, in which a hydrogen atom of the benzene ring in the formula (2C) may be substituted with a methyl group or a methoxy group,

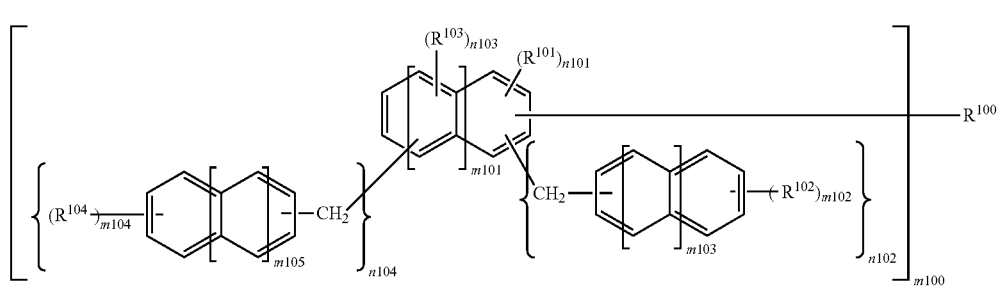

wherein $R^{101}$, $R^{102}$, $R^{103}$, and $R^{104}$ independently represent a hydroxyl group; m100 represents 1, 2, or 3; $R^{100}$ represents a hydrogen atom or a hydroxyl group when m100 is 1, $R^{100}$ represents a single bond or a group shown by the formula (3B) when m100 is 2, and $R^{100}$ represents a group shown by the formula (3C) when m100 is 3; a hydrogen atom of the aromatic ring in the formula (3A) may be substituted with a methyl group, a methoxy group, a hydroxymethyl group, or a methoxymethyl group; m101 represents 0 or 1, m102 represents 1 or 2; m103 represents 0 or 1; m104 represents 1 or 2; m105 represents 0 or 1; when m101 is 0, n101 and n102 represent an integer satisfying $0 \leq n101 \leq 3$, $0 \leq n102 \leq 3$, and $1 \leq n101+n102 \leq 4$, and when m101 is 1, n101, n102, n103, and n104 represent an integer satisfying $0 \leq n101 \leq 2$, $0 \leq n102 \leq 2$, $0 \leq n103 \leq 2$, $0 \leq n104 \leq 2$, and $2n101+n102+n103+n104 \leq 8$,

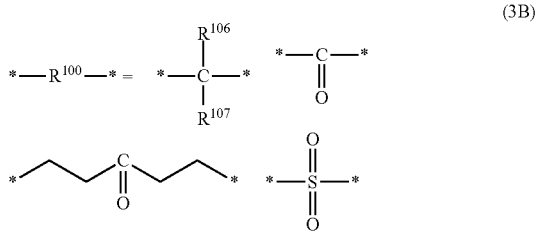

wherein * represents a bonding site; $R^{106}$ and $R^{107}$ represent a hydrogen atom or an organic group having 1 to 24 carbon atoms, and $R^{106}$ and $R^{107}$ may be bonded to form a cyclic structure,

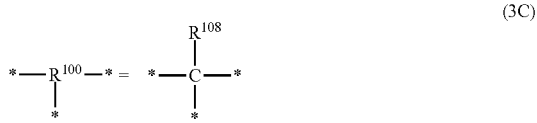

wherein * represents a bonding site; and $R^{108}$ represents a hydrogen atom or an organic group having 1 to 15 carbon atoms.

5. The composition for forming an organic film according to claim 3, wherein the organic solvent is a mixture of one or more organic solvents having a boiling point of lower than 180° C. and one or more organic solvents having a boiling point of 180° C. or higher.

6. A method for forming an organic film that functions as an organic planarizing film used in a semiconductor apparatus manufacturing process, the method comprising: applying the composition for forming an organic film according to claim 3 on a substrate to be processed by spin coating; and heating the substrate, on which the composition has been applied, at 100° C. to 600° C. for 10 to 600 seconds to form a cured film.

7. The method for forming an organic film according to claim 6, wherein the substrate to be processed has steps or a structure with a height of 30 nm or more.

8. A method for forming an organic film that functions as an organic planarizing film used in a semiconductor apparatus manufacturing process, the method comprising: applying the composition for forming an organic film according to claim 3 on a substrate to be processed by spin coating; and heating the substrate, on which the composition has been applied, under an atmosphere having an oxygen concentration of 0.1% to 21% to form a cured film.

9. A patterning process comprising: forming an organic film on a body to be processed from the composition for forming an organic film according to claim 3; forming a resist underlayer film on the organic film from a resist underlayer film composition containing a silicon atom; forming a resist upper layer film on the resist underlayer film from a resist upper layer film composition composed of a photoresist composition; forming a circuit pattern in the resist upper layer film; transferring the pattern to the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

10. The patterning process according to claim 9, the circuit pattern is formed by a photolithography with a wavelength ranging from 10 nm to 300 nm, a direct drawing with electron beam, a nanoimprinting, or a combination thereof.

11. The patterning process according to claim 9, the circuit pattern is developed by alkaline development or development with an organic solvent.

12. The patterning process according to claim 9, wherein the body to be processed is a semiconductor apparatus substrate or the semiconductor apparatus substrate coated with any of a metal film, a metal carbide film, a metal oxide film, a metal nitride film, a metal oxycarbide film, and a metal oxynitride film.

13. The patterning process according to claim 12, wherein the metal of the body to be processed is silicon, titanium, tungsten, hafnium, zirconium, chromium, germanium, copper, silver, gold, aluminum, indium, gallium, arsenic, palladium, iron, tantalum, iridium, molybdenum, or an alloy thereof.

14. A patterning process comprising: forming an organic film on a body to be processed from the composition for forming an organic film according to claim 3; forming a resist underlayer film on the organic film from a resist underlayer film composition containing a silicon atom; forming an organic antireflective film on the resist underlayer film; forming a resist upper layer film on the organic antireflective film from a resist upper layer film composition composed of a photoresist composition; forming a circuit pattern in the resist upper layer film; transferring the pattern to the organic antireflective film and the resist underlayer film by etching using the resist upper layer film having the formed circuit pattern as a mask; transferring the pattern to the organic film by etching using the resist underlayer film having the transferred pattern as a mask; and further transferring the pattern to the body to be processed by etching using the organic film having the transferred pattern as a mask.

15. A patterning process comprising: forming an organic film on a body to be processed from the composition for forming an organic film according to claim 3; forming an inorganic hard mask selected from a silicon oxide film, a silicon nitride film, and a silicon oxynitride film on the organic film; forming a resist upper layer film on the inorganic hard mask from a resist upper layer film composition composed of a photoresist composition; forming a circuit pattern in the resist upper layer film; transferring the pattern to the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

16. The patterning process according to claim 15, wherein the inorganic hard mask is formed by a CVD method or an ALD method.

17. A patterning process comprising: forming an organic film on a body to be processed from the composition for forming an organic film according to claim 3; forming an inorganic hard mask selected from a silicon oxide film, a silicon nitride film, and a silicon oxynitride film on the organic film; forming an organic antireflective film on the inorganic hard mask; forming a resist upper layer film on the organic antireflective film from a resist upper layer film composition composed of a photoresist composition; forming a circuit pattern in the resist upper layer film; transferring the pattern to the organic antireflective film and the inorganic hard mask by etching using the resist upper layer film having the formed circuit pattern as a mask; transferring the pattern to the organic film by etching using the inorganic hard mask having the transferred pattern as a mask; and further transferring the pattern to the body to be processed by etching using the organic film having the transferred pattern as a mask.

* * * * *